(12) United States Patent
Scholl et al.

(10) Patent No.: US 8,361,145 B2
(45) Date of Patent: Jan. 29, 2013

(54) ACCOMMODATING INTRAOCULAR LENS SYSTEM HAVING CIRCUMFERENTIAL HAPTIC SUPPORT AND METHOD

(75) Inventors: John Scholl, San Ramon, CA (US);
Terah Smiley, San Francisco, CA (US);
David J. Smith, Highland, CA (US);
Denise H. Burns, Sunnyvale, CA (US);
Barry Cheskin, Mountain View, CA (US)

(73) Assignee: PowerVision, Inc., Belmont, CA (US)

( * ) Notice: Subject to any disclaimer, the term of this patent is extended or adjusted under 35 U.S.C. 154(b) by 1226 days.

(21) Appl. No.: 11/642,388

(22) Filed: Dec. 19, 2006

(65) Prior Publication Data

US 2007/0203578 A1 Aug. 30, 2007

Related U.S. Application Data

(63) Continuation-in-part of application No. 10/971,598, filed on Oct. 22, 2004, now Pat. No. 7,261,737, which is a continuation-in-part of application No. 10/734,514, filed on Dec. 12, 2003, now Pat. No. 7,122,053.

(60) Provisional application No. 60/433,046, filed on Dec. 12, 2002.

(51) Int. Cl.
*A61F 2/16* (2006.01)

(52) U.S. Cl. ..................................... 623/6.13

(58) Field of Classification Search ................... 623/4.1, 623/6.11, 6.13, 6.22, 6.37–6.41
See application file for complete search history.

(56) References Cited

U.S. PATENT DOCUMENTS

| | | | |
|---|---|---|---|
| 4,111,995 A | 9/1978 | Nelson | |
| 4,253,199 A | 3/1981 | Banko | |
| 4,254,509 A | 3/1981 | Tennant | |
| 4,304,895 A | 12/1981 | Loshaek | |
| 4,373,218 A | 2/1983 | Schachar | |
| 4,409,691 A | 10/1983 | Levy | |
| 4,423,809 A | 1/1984 | Mazzocco | |
| 4,435,856 A | 3/1984 | L'Esperance | |
| 4,466,705 A | 8/1984 | Michelson | |
| 4,490,860 A | 1/1985 | Rainin | |
| 4,494,254 A | 1/1985 | Lopez | |
| 4,512,040 A | 4/1985 | McClure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A | 10/1986 | Woods | |
| 4,620,954 A | 11/1986 | Singer et al. | |
| 4,685,921 A | 8/1987 | Peyman | |
| 4,685,922 A | 8/1987 | Peyman | |

(Continued)

FOREIGN PATENT DOCUMENTS

| EP | 0898972 A2 | 3/1999 |
|---|---|---|
| FR | 2784575 | 4/2000 |

(Continued)

OTHER PUBLICATIONS

Smiley et al.; U.S. Appl. No. 12/178,565 entitled "Lens delivery system," filed Jul. 23, 2008.

(Continued)

*Primary Examiner* — William H. Matthews
(74) *Attorney, Agent, or Firm* — Shay Glenn LLP

(57) ABSTRACT

An accommodating intraocular lens includes an optic portion a haptic portion and a backstop. The optic portion of the lens includes an actuator that deflects a lens element to alter the optical power of the lens responsive to forces applied to the haptic portion of the lens by contraction of the ciliary muscles. Forces applied to the haptic portion may result in fluid displacements from or to the haptic portion from the actuator. The backstop provides support to the haptic so that bulk translation of the haptic is prevented in response to the forces applied by the capsular sac.

9 Claims, 22 Drawing Sheets

U.S. PATENT DOCUMENTS

| | | |
|---|---|---|
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,171,266 A | 12/1992 | Wiley et al. |
| 5,200,430 A | 4/1993 | Federman |
| 5,201,763 A | 4/1993 | Brady et al. |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,843,188 A | 12/1998 | McDonald |
| 5,891,931 A | 4/1999 | Leboeuf et al. |
| 5,928,282 A | 7/1999 | Nigam |
| 5,964,802 A | 10/1999 | Anello et al. |
| 5,984,962 A | 11/1999 | Anello et al. |
| 6,013,101 A | 1/2000 | Israel |
| 6,015,842 A | 1/2000 | LeBoeuf et al. |
| 6,102,539 A | 8/2000 | Tucker |
| 6,117,171 A | 9/2000 | Skottum |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,966,649 B2 | 11/2005 | Shadduck |
| 6,969,403 B2 | 11/2005 | Peng et al. |
| 7,060,094 B2 | 6/2006 | Shahinpoor et al. |
| 7,068,439 B2 | 6/2006 | Esch |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,689 B2 | 7/2007 | Makker et al. |
| 7,264,351 B2 | 9/2007 | Shadduck |
| 7,276,619 B2 | 10/2007 | Kunzler et al. |
| 7,278,739 B2 | 10/2007 | Shadduck |

| | | |
|---|---|---|
| 7,311,194 B2 | 12/2007 | Jin et al. |
| 7,416,300 B2 | 8/2008 | Wei et al. |
| 7,453,646 B2 | 11/2008 | Lo |
| 7,494,505 B2 | 2/2009 | Kappelhof et al. |
| 7,675,686 B2 | 3/2010 | Lo et al. |
| 7,759,408 B2 | 7/2010 | Schorzman et al. |
| 7,763,069 B2 | 7/2010 | Brady et al. |
| 7,988,292 B2 | 8/2011 | Neal et al. |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0190153 A1 | 9/2004 | Esch |
| 2004/0230203 A1 | 11/2004 | Yaguchi |
| 2005/0021139 A1 | 1/2005 | Shadduck |
| 2005/0119740 A1 | 6/2005 | Esch et al. |
| 2005/0131535 A1 | 6/2005 | Woods |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1 | 2/2006 | Esch et al. |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0183041 A1 | 8/2006 | Erk et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0010880 A1 | 1/2007 | Esch |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0129801 A1 | 6/2007 | Cumming |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Ben Nun |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0027537 A1 | 1/2008 | Gerlach et al. |
| 2008/0035243 A1 | 2/2008 | Breitenkamp et al. |
| 2008/0097460 A1 | 4/2008 | Boukhny et al. |
| 2008/0139769 A1 | 6/2008 | Iwamoto et al. |
| 2008/0269887 A1 | 10/2008 | Cumming |
| 2008/0300680 A1 | 12/2008 | Joshua |
| 2009/0312836 A1 | 12/2009 | Pinchuk et al. |
| 2010/0039709 A1 | 2/2010 | Lo |
| 2010/0228344 A1 | 9/2010 | Shadduck |
| 2010/0228346 A1 | 9/2010 | Esch |
| 2011/0118834 A1 | 5/2011 | Lo et al. |
| 2012/0078364 A1 | 3/2012 | Stenger |
| 2012/0179249 A1 | 7/2012 | Coleman |

FOREIGN PATENT DOCUMENTS

| | | |
|---|---|---|
| JP | 02-167157 | 6/1990 |
| JP | 07-044938 | 5/1995 |
| JP | 9294754 | 11/1997 |
| JP | 10-206609 | 8/1998 |
| JP | 11276509 | 10/1999 |
| SU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 | 2/2004 |
| WO | WO 2004/046768 A2 | 6/2004 |
| WO | WO 2004/052242 A1 | 6/2004 |
| WO | WO 2004/054471 A3 | 7/2004 |
| WO | WO 2004/072689 A2 | 8/2004 |
| WO | WO 2005/084588 A1 | 9/2005 |
| WO | WO 2006/004707 A2 | 1/2006 |
| WO | WO2006011937 A2 | 2/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/030095 A1 | 3/2007 |
| WO | WO 2007/061688 A2 | 5/2007 |
| WO | WO 2007/128423 A1 | 11/2007 |
| WO | WO2007/138564 A1 | 12/2007 |

OTHER PUBLICATIONS

Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; 2002.

Esch et al; U.S. Appl. No. 11/844,108 entitled "Accommodating Intraocular Lens System and Method" filed Aug. 23, 2007.

Smith et al; U.S. Appl. No. 11/844,087 entitled "Accommodating Intraocular Lens System Having Spherical Aberration Compensation and Method," filed Aug. 23, 2007.

Wyant et al; "Basic Wavefront Aberration Theory for Optical Metrology," Applied Optics and Optical Engineering, vol. XI, 1992:1-13.

Shadduck, John H.; U.S. Appl. No. 12/347,816 entitled "Intraocular lenses and business methods," filed Dec. 31, 2008.

Gruber et al.; Exhaustive soxhlet extraction for the complete removal of residual compounds . . . ; Journal of Biomedical Materials Research; vol. 53; No. 5; pp. 445-448; Mar. 2000.

Shadduck, John H.; U.S. Appl. No. 12/694,184 entitled "Intraocular Lenses and Business Methods," filed Jan. 26, 2010.

Argento et al.; U.S. Appl. No. 12/685,531 entitled "Intraocular Lenses and Methods of Accounting for Capsule Size Variability and Post-Implant Changes in the Eye," filed Jan. 11, 2010.

Baughman et al., "Negative poisson's ratios for extreme states fo matter," Science, vol. 288, pp. 1028-2022, Jun. 16, 2000.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Lakes et al., "Microbuckling instability in elastomeric cellular sollids," J. Materials Science, vol. 28, pp. 4667-4672, 1993.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Xu et al., "Basic negative poisson's ratio microstructures by soft lithography," Advanced Materials, vol. 11, No. 14, 1999, pp. 1186-1189, 1999.

Your, Jingjong; U.S. Appl. No. 12/034,942 entitled "Polymeric materials suitable for ophthalmic devices and methods of manufacture," filed Feb. 21, 2008.

Your, Jingjong; U.S. Appl. No. 12/177,720 entitled "Lens material and methods of curing with UV light," filed Jul. 22, 2008.

Smiley et al.; U.S. Appl. No. 12/177,857 entitled "Accommodating intraocular lenses and methods of use," filed Jul. 22, 2008.

Smiley et al.; U.S. Appl. No. 12/178,304 entitled "Post-implant accommodating lens modification," filed Jul. 23, 2008.

Choi et al.; U.S. Appl. No. 12/178,454 entitled "Systems and methods for testing intraocular lenses," filed Jul. 23, 2008.

Shadduck, John H.; U.S. Appl. No. 12/852,733 entitled "Intraocular Lens System and Method for Power Adjustment," filed Aug. 9, 2010.

Esch et al.; U.S. Appl. No. 12/853,892 entitled "Accommodating Intraocular Lens Having Peripherally Actuated Deflectable Surface and Method," filed Aug. 10, 2010.

Hildebrand et al.; U.S. Appl. No. 12/872,314 entitled "Lens Capsule Size Estimation," filed Aug. 31, 2010.

Baughman, "Avoiding the shrink," Nature, vol. 425, pp. 667, Oct. 16, 2003.

Conlisk, A. T. et al; Mass Transfer and Flow in Electrically Charged Micro- and Nano-channels; Analytical Chemistry, vol. 74; iss. 9; pp. 2139-2150; 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Metcalfe et al., "Cold hibernated elastic memory foams for endovascular interventions," Biomaterials, vol. 24, pp. 491-497, 2003.

Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.

Vass et al.; Prediction of pseudophakic capsular bag diameter based on biometric variables; J Cataract Refract Surg.; vol. 25; pp. 1376-1381; 1999.

Wang et al., "Deformation of extreme viscoelastic metals and composites," Materials Science and Enginerring A, vol. 370, pp. 41-49, 2004.

Wang et al., "Extreme stiffness systems due to negative stiffness elements," American Journal of Physics, vol. 72, No. 1, pp. 40-50, Jan. 2004.

Wang et al., "Stable extremely-high-damping discrete viscoelastic systems due to native stiffness elements," Applied Physics Letters, vol. 84, No. 22, pp. 4451-4453, May 31, 2004.

Anvar et al.; U.S. Appl. No. 13/033,474 entitled "Fluid for Accommodating Intraocular Lenses," filed Feb. 23, 2011.

Shadduck, John H.; U.S. Appl. No. 13/300,245 entitled "Accommodating Intraocular Lenses and Methods of Use," filed Nov. 18, 2011.

Scholl et al.; U.S. Appl. No. 13/193,487 entitled "Accommodating Intraocular Lenses," filed Jul. 28, 2011.

Smiley et al.; U.S. Appl. No. 13/193,983 entitled "Accommodating Intraocular Lenses," filed Jul. 29, 2011.

Smiley et al.; U.S. Appl. No. 13/194,004 entitled "Accommodating Intraocular Lenses," filed Jul. 29, 2011.

Hildebrand et al.; U.S. Appl. No. 13/180,427 entitled "Intraocular lens delivery devices and methods of use," filed Jul. 11, 2011.

Matthews, Gregory V.; U.S. Appl. No. 13/427,617 entitled "Intraocular Lens Loading Systems and Methods of Use," filed Mar. 22, 2012.

USPTO, "Office Action," corresponding U.S. Appl. No. 12/782,639, mailed Jan. 9, 2012, 33 pages.

USPTO, "Office Action," corresponding U.S. Appl. No. 12/853,892, mailed Jan. 9, 2012, 31 pages.

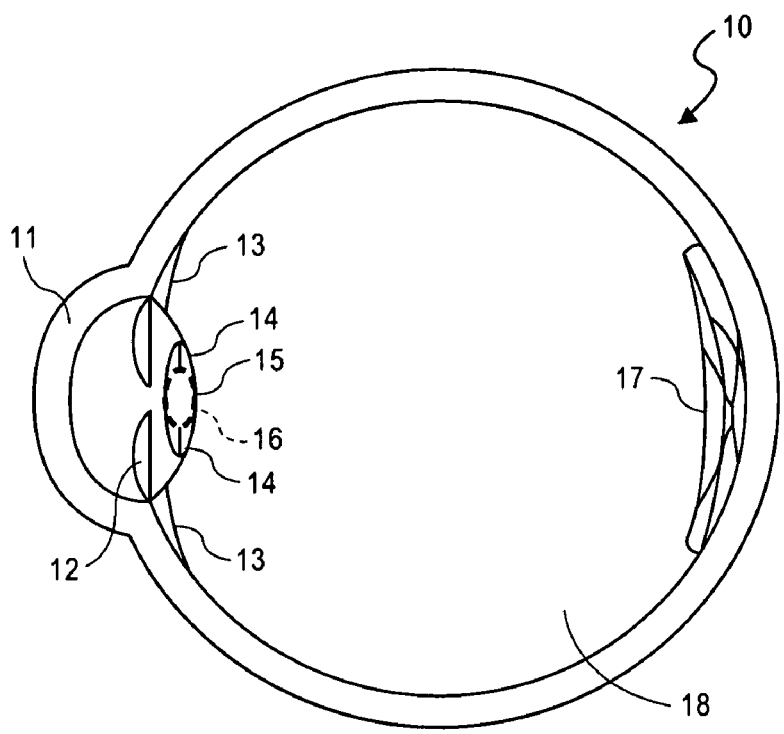
FIG. 1
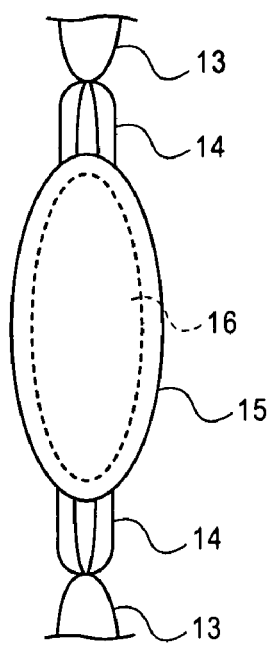  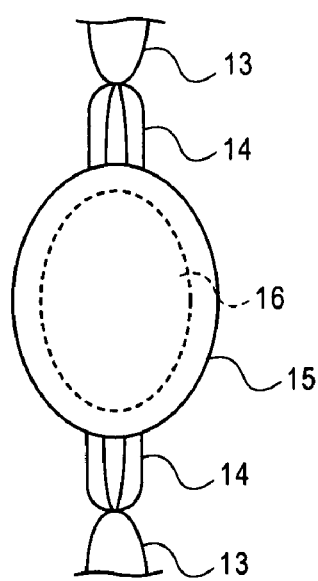
FIG. 2A        FIG. 2B

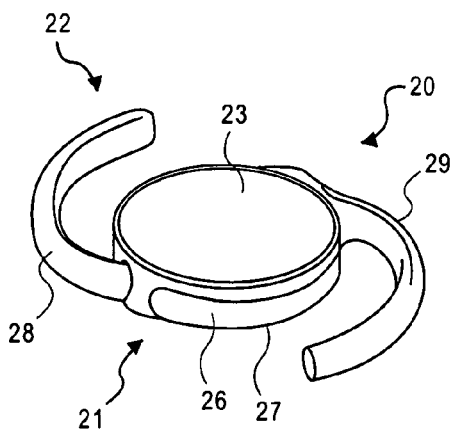
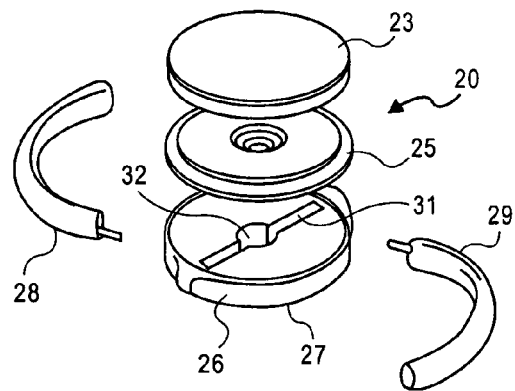
FIG. 3A  FIG. 3B
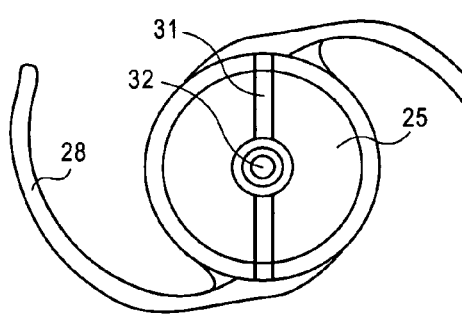
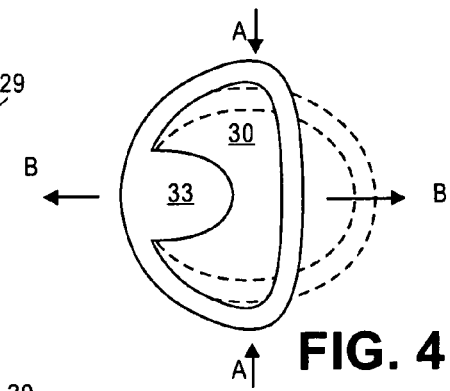
FIG. 3C  FIG. 4
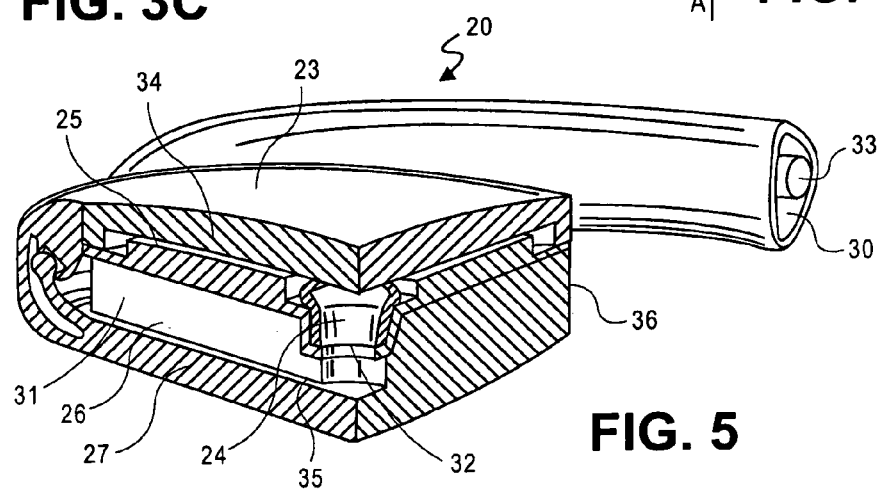
FIG. 5

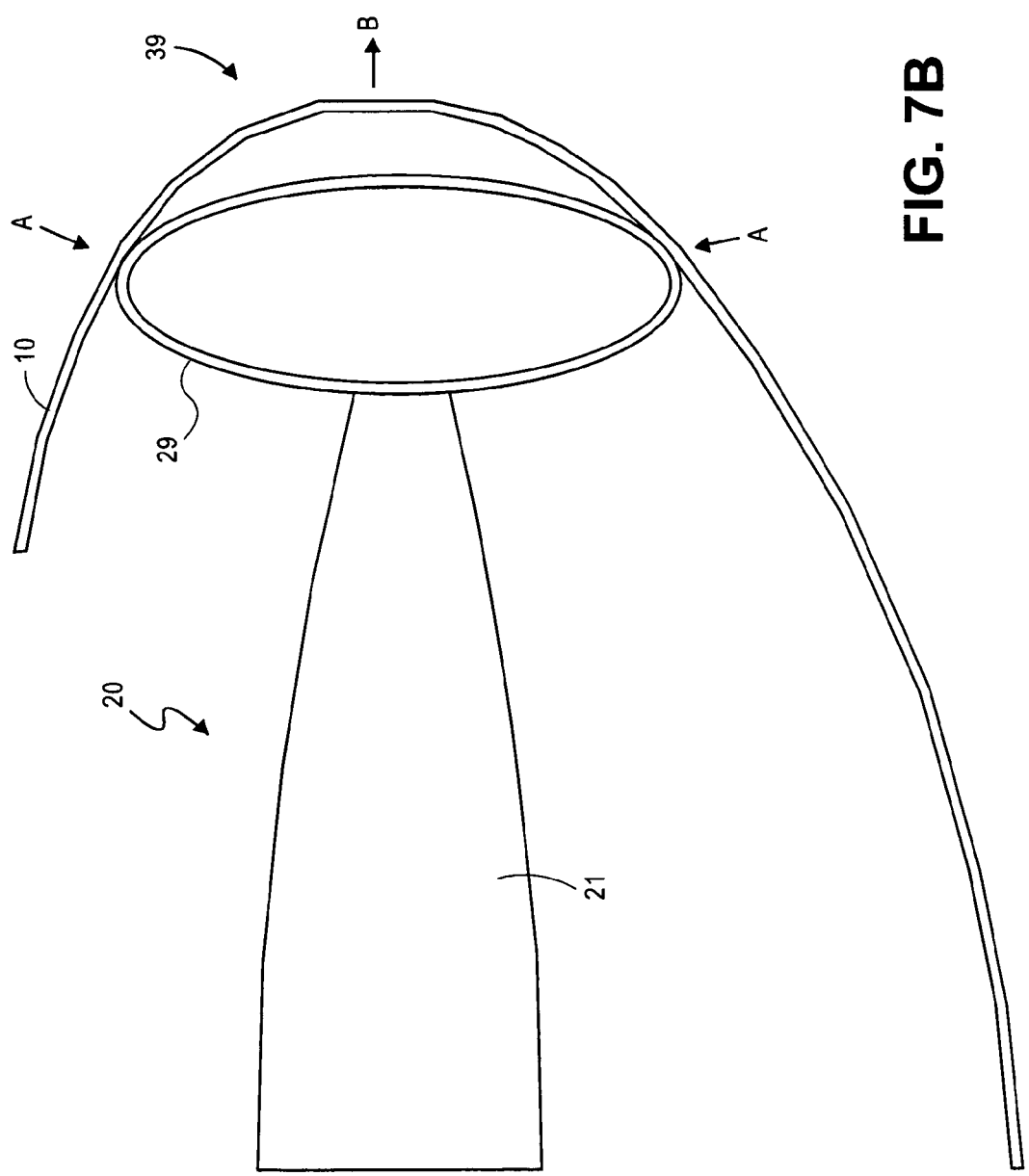

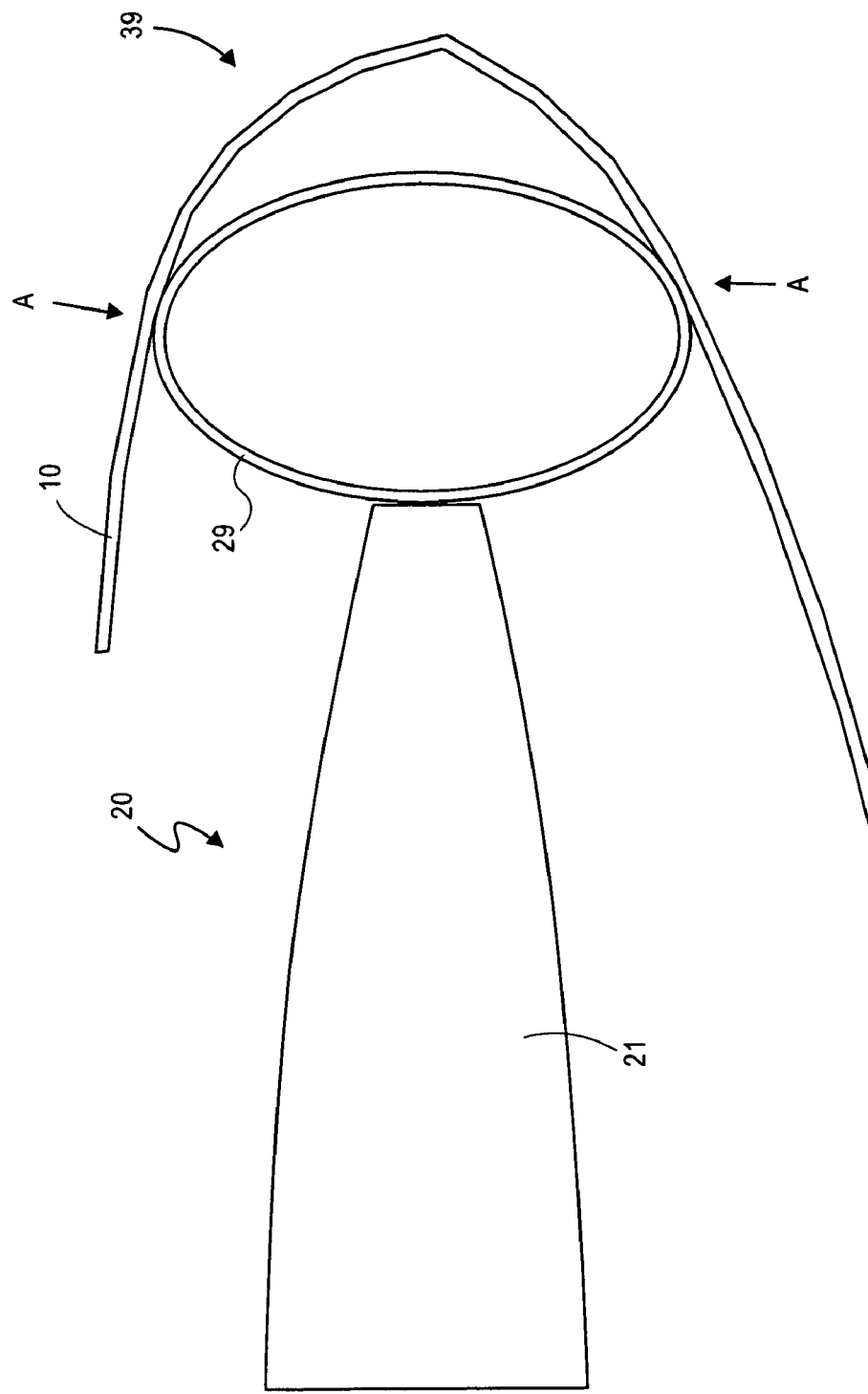

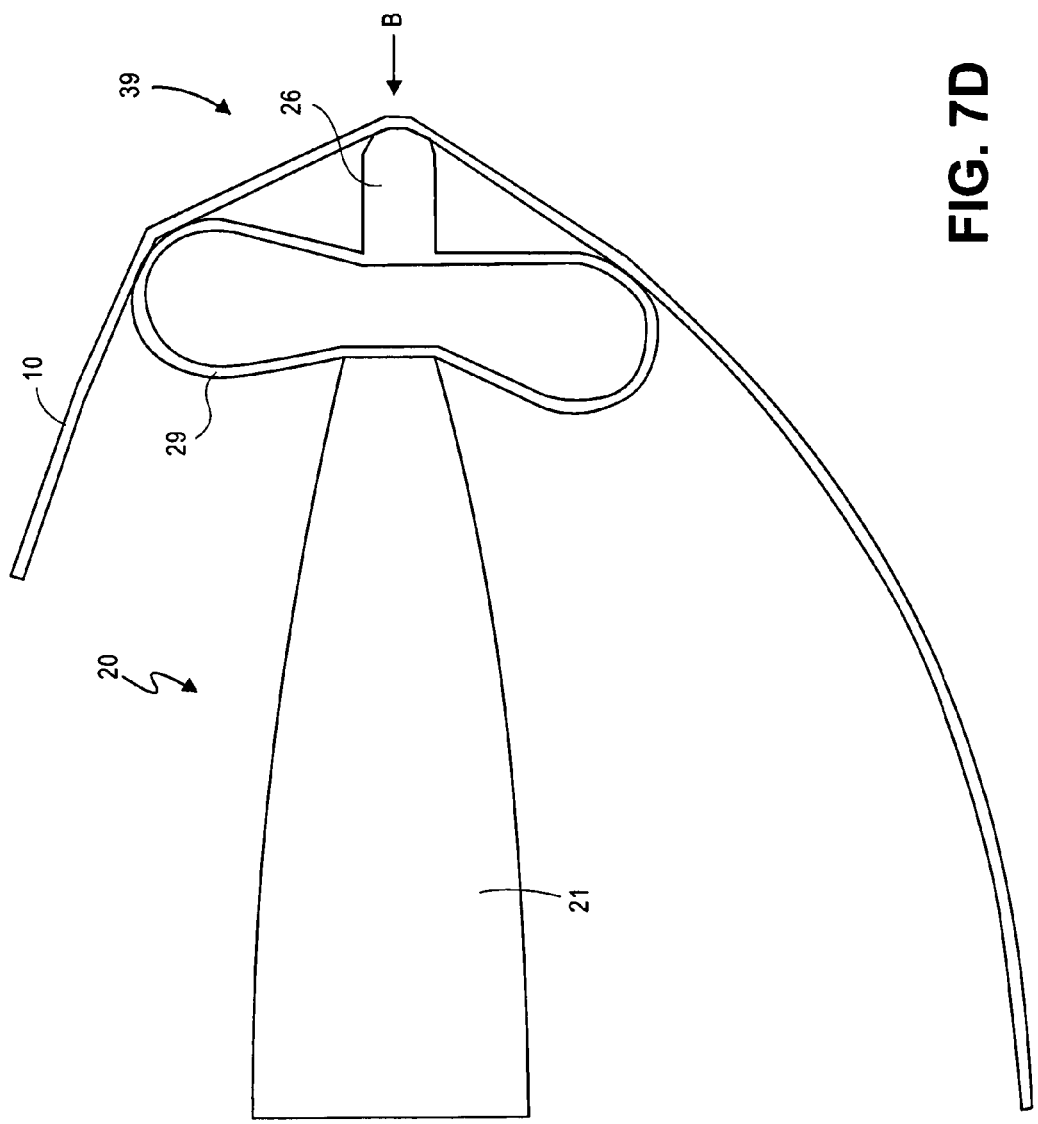

US 8,361,145 B2

ACCOMMODATING INTRAOCULAR LENS SYSTEM HAVING CIRCUMFERENTIAL HAPTIC SUPPORT AND METHOD

REFERENCE TO RELATED APPLICATION

This application is a continuation-in-part of U.S. patent application Ser. No. 10/971,598, filed Oct. 22, 2004 and now U.S. Pat. No. 7,261,737, which is a continuation-in-part of U.S. patent application Ser. No. 10/734,514, filed Dec. 12, 2003 and now U.S. Pat. No. 7,122,053, and claims the benefit of priority from U.S. provisional patent application Ser. No. 60/433,046, filed Dec. 12, 2002, the disclosures of which are hereby incorporated by reference in their entirety.

FIELD OF THE INVENTION

The present invention relates to intraocular lenses ("IOLs") having optical parameters that are changeable in-situ. More particularly, the invention has application in IOLs for in-capsule implantation for cataract patients or presbyopic patients, wherein movement of the lens capsule applies forces to a circumferentially supported haptic to more efficiently induce transfer of fluid media within the interior of the IOL to alter an optical power of the lens.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule supported by the ciliary muscles via zonules, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein) move between a relaxed state (corresponding to the moderately convex shape) and a contracted state (corresponding to the highly convex shape). Because the lens itself is composed of viscous, gelatinous transparent fibers, arranged in an "onion-like" layered structure, forces applied to the capsule by the ciliary muscles via the zonules cause the lens to change shape.

Isolated from the eye, the relaxed capsule and lens take on a more spherical, or more convex, shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape (i.e., more convex shape).

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition known as "presbyopia". Because the imaging distance is fixed, presbyopia typically entails the need for bi-focals to facilitate near and far vision.

Apart from age-related loss of accommodation ability, such loss is innate to the placement of IOLs for the treatment of cataracts. IOLs are generally single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability.

Although previously known workers in the field of accommodating IOLs have made some progress, the relative complexity of the methods and apparatus developed to date have prevented widespread commercialization of such devices. Previously known devices have proved too complex to be practical to construct or have achieved only limited success, due to the inability to provide accommodation of more than 1-2 diopters.

U.S. Pat. No. 5,443,506 to Garabet describes an accommodating fluid-filled lens wherein electrical potentials generated by contraction of the ciliary muscles cause changes in the index of refraction of fluid carried within a central optic portion. U.S. Pat. No. 4,816,031 to Pfoff discloses an IOL with a hard poly methyl methacrylate (PMMA) lens separated by a single chamber from a flexible thin lens layer that uses microfluid pumps to vary a volume of fluid between the PMMA lens portion and the thin layer portion and provide accommodation. U.S. Pat. No. 4,932,966 to Christie et al. discloses an intraocular lens comprising a thin flexible layer sealed along its periphery to a support layer, wherein forces applied to fluid reservoirs in the haptics vary a volume of fluid between the layers to provide accommodation.

Although fluid-actuated mechanisms such as described in the aforementioned patents have been investigated, currently available accommodating lenses include the Crystalens developed by Eyeonics, Inc. (formerly C&C Vision, Inc.) of Aliso Viejo, Calif. According to Eyeonics, redistribution of the ciliary mass upon constriction causes increased vitreous pressure resulting in forward movement of the lens.

Co-pending, commonly assigned U.S. Patent Application Publication No. 2005/0119740 to Esch et al., which is incorporated by reference herein in its entirety, describes an intraocular lens in which forces applied by the lens capsule to a haptic portion of the lens to induce fluid transfer to and from an actuator disposed in contact with a dynamic surface of the lens.

While the lens described in the foregoing Esch application is expected to provide significant benefits over previously-known accommodating lens designs, it would be desirable to provide methods and apparatus for further enhancing conversion of lens capsule movements into hydraulic forces, so as to improve modulation of the lens actuator and dynamic surface.

It also would be desirable to provide methods and apparatus to enhance the efficiency with which loads arising due to natural accommodating muscular action are converted to hydraulic forces.

SUMMARY OF THE INVENTION

In view of the foregoing, it is an object of the present invention to provide apparatus and methods that restore appropriate optical focusing power to the human eye.

It is a further object of this invention to provide methods and apparatus wherein a dynamic lens surface may be hydraulically manipulated responsive to movement of the ciliary muscles and lens capsule.

It also is an object of the present invention to provide methods and apparatus for further enhancing conversion of lens capsule movements into hydraulic forces, so as to improve modulation of the lens actuator and dynamic surface.

It is another object of this invention to provide methods and apparatus to enhance the efficiency with which loads arising due to natural accommodating muscular action are converted to hydraulic forces.

These and other objects of the present invention are accomplished by providing an intraocular lens responsive to forces communicated from the ciliary muscles through the zonules to the capsular bag to operate one or more actuators disposed within the IOL. The actuator is coupled to a dynamic surface of the IOL to deflect the dynamic surface, e.g., from a moderately convex to a highly convex shape, responsive to operation of the one or more actuators.

In accordance with the principles of the present invention, the IOL includes at least one fluid-mediated actuator coupled to a fluid column disposed in at least one haptic of the IOL and a haptic support structure, or backstop, supporting at least a portion of the haptic. Forces applied to the haptic by the capsular bag, responsive to movement of the ciliary muscles, cause the transfer of fluid between the fluid column and the actuator, which in turn deflects a dynamic surface of the lens. As used herein, a "backstop" is a structure that opposes the forces applied by the capsular sac and limits or prevents bulk translation of the entire haptic in response to those forces so that the force may be converted more efficiently into deformation of the haptic. The backstop may be integrated into an optic portion or a haptic portion of the IOL or a separate structure.

In a preferred embodiment, the intraocular lens comprises an optic portion, a haptic (or non-optic) portion and a backstop. The optic portion comprises a light transmissive substrate defining one or more fluid channels, at least one actuator coupled in fluid communication with the fluid channels, and anterior and posterior lens elements. One of the anterior and posterior lens elements includes a dynamic surface that is operatively coupled to the actuator to cause deflection of the dynamic surface. The other of the anterior or posterior lens elements may be coupled to the substrate or integrally formed therewith as a monolithic body.

The haptic portion is disposed at the periphery of the optic portion and comprises one or more haptics that extend outward from the optic portion, each haptic including a fluid channel coupled in fluid communication with a fluid channel in the optic portion. In accordance with one aspect of the present invention, the haptics have a cross-sectional configuration selected so that the internal volume of the haptic is small in an accommodated state. The accommodated state of the eye corresponds to the condition when the ciliary muscles are contracted and anterior/posterior (i.e., axial) compressive forces applied by the capsular bag to the haptics are minimal and radial compressive forces applied by the capsular bag compress the haptic radially toward the optical axis.

When the ciliary muscles relax, the zonules pull the capsular bag taut and apply forces to the anterior and posterior faces of the haptic and reduce the compressive forces applied radially to the haptic. The backstop prevents the entire haptic from translating in response to these forces. The backstop may be configured to resist bulk axial or radial translation of the haptic or combinations thereof. The forces applied by the capsular bag in conjunction with the backstop cause the cross-sectional area of the haptic to increase thereby increasing the internal volume of the haptic. This action in turn causes fluid to be withdrawn from the actuator disposed in the optic portion, so that the dynamic surface of the IOL transitions from an accommodated state to an unaccommodated state.

The actuator used in the optic portion of the IOL may be centrally located within the optic portion that, when filled with fluid, biases the dynamic surface of the IOL to the accommodated state. When the ciliary muscles are contracted, the zonules and capsular bag are less taut, and the haptics are compressed radially toward the optical axis. Relaxation of the ciliary muscle causes the zonules to transition the capsule to less convex shape, which applies compressive forces to the posterior and anterior faces of the haptic, thereby withdrawing fluid from the actuator and causing the lens to transition to the unaccommodated state. Alternatively, the actuator may comprise structures disposed at the periphery of the optic portion, so as to minimize refractive effects and optical aberrations in the optic portion.

In another embodiment, the backstop is a thin-walled member that is coupled to a portion of an outer surface of the haptic, radially spaced from the optic portion of the IOL. Alternatively, the backstop may extend radially outward from the optic portion to the haptic portion. The backstop is generally shaped as a portion of a disk or cone, and may be configured to tangentially support a haptic, or it may be configured to support a portion of the outer surface of the haptic.

Methods of making and using the lens of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIG. 1 is a sectional side view of a human eye;

FIGS. 2A and 2B are, respectively, sectional side views of the lens and supporting structures of FIG. 1 illustrating relaxed and contracted states of the ciliary muscles;

FIGS. 3A-3C are, respectively, a perspective, exploded perspective and plan view of an exemplary intraocular lens which may be modified to implement the structure and methods of the present invention;

FIG. 4 is a cross-sectional view of a haptic of the intraocular lens of FIGS. 3;

FIG. 5 is a cross-sectional view of the assembled intraocular lens of FIGS. 3;

FIGS. 7A-7D are schematic cross-sectional views of the interaction between a lens capsule and an intraocular lens;

FIGS. 10A-10C are cross-sectional schematic views of a backstop and a haptic, wherein FIGS. 10A and 10B show alternative embodiments in an accommodated state and FIG. 10C shows an embodiment in an unaccommodated state;

FIGS. 12A-12D are cross-sectional schematic views of a backstop and a haptic, wherein FIGS. 12A-12C show alternative embodiments in an accommodated state and FIG. 12D shows an embodiment in an unaccommodated state.

DETAILED DESCRIPTION OF THE INVENTION

Figure 6A:
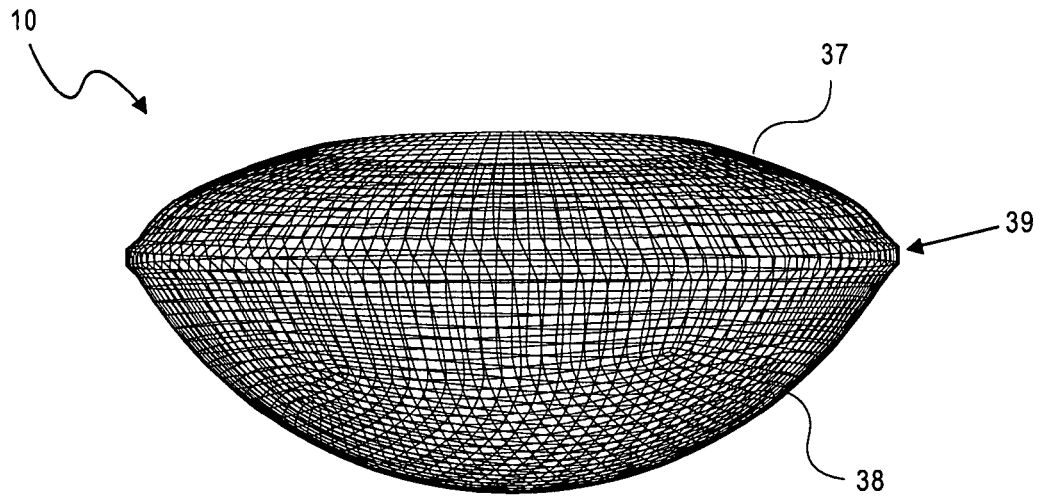
FIGS. 6A-6C are graphical representations of a lens capsule in accommodated, transition and unaccommodated configurations, respectively.

In accordance with the principles of the present invention, an intraocular lens is provided having a haptic portion and a light-transmissive optic portion. The optic portion contains one or more fluid-mediated actuators arranged to apply a deflecting force on a dynamic surface of the lens to provide accommodation. As used herein, the lens is fully "accommodated" when it assumes its most highly convex shape, and fully "unaccommodated" when it assumes its most flattened, least convex state. The lens of the present invention is capable of dynamically assuming any desired degree of accommodation between the fully accommodated state and fully unaccommodated state responsive to movement of the ciliary muscles and lens capsule.

Forces applied to a haptic portion of the intraocular lens by movement of the ciliary muscles and lens capsule are communicated to at least one actuator that controls deflection of a dynamic surface, which may comprise an anterior or posterior element of the lens. In accordance with the principles of the present invention, the haptic portion is supported over at least a portion of its circumference to efficiently convert movements of the lens capsule into hydraulic forces suitable for moving the lens actuator. The lens actuator and surrounding fluids all are index-matched to prevent the occurrence of optical aberrations and reflections throughout the range of motion of the actuator and dynamic surface.

Referring to FIGS. 1 and 2, the structure and operation of a human eye are first described as context for the present invention. Eye 10 includes cornea 11, iris 12, ciliary muscles 13, ligament fibers or zonules 14, capsule 15, lens 16 and retina 17. Natural lens 16 is composed of viscous, gelatinous transparent fibers, arranged in an "onion-like" layered structure, and is disposed in transparent elastic capsule 15. Capsule 15 is joined by zonules 14 around its circumference to ciliary muscles 13, which are in turn attached to the inner surface of eye 10. Vitreous 18 is a viscous, transparent fluid that fills the center of eye 10.

Isolated from the eye, the relaxed capsule and lens take on a highly convex shape. However, when suspended within the eye by zonules 14, capsule 15 moves between a moderately convex shape (when the ciliary muscles are relaxed) and a highly convex shape (when the ciliary muscles are contracted). As depicted in FIG. 2A, when ciliary muscles 13 relax, capsule 15 and lens 16 are pulled about the circumference, thereby flattening the lens. As depicted in FIG. 2B, when ciliary muscles 13 contract, capsule 15 and lens 16 relax and become thicker. This allows the lens and capsule to assume a more convex shape, thus increasing the diopter power of the lens.

Accommodating lenses that are currently commercially available, such as the Crystalens device developed by Eyeonics, Inc., Aliso Viejo, Calif., typically involve converting movements of the ciliary muscle into anterior and posterior movement of an optic portion of the IOL relative to the retina. Such devices do not employ the natural accommodation mechanisms described above with respect to FIGS. 1-2, but instead rely directly on changes in vitreous pressure to translate the lens.

Referring now to FIGS. 3-5, an exemplary embodiment of an intraocular lens suitable for implementing the structure of the present invention is described, such as is described in the commonly assigned U.S. Patent Application No. 2005/0119740 to Esch et al., which is incorporated herein by reference. For completeness of disclosure, details of the IOL described in that application are provided below.

IOL 20 comprises optic portion 21 and haptic portion 22. Optic portion 21 is constructed of light transmissive materials, while haptic portion 22 is disposed at the periphery of the optic portion and does not participate in focusing light on the retina of the eye.

Optic portion 21 comprises anterior lens element 23 including actuator 24 (see FIG. 5), intermediate layer 25 and posterior lens element 27, also referred to herein as "substrate," all made of light-transmissive materials, such as silicone or acrylic polymers or other biocompatible materials as are known in the art of intraocular lenses. Illustratively, actuator 24 comprises a bellows structure that is integrally formed with anterior lens element 23. It will be appreciated that actuator 24 may alternatively be integrally formed with intermediate layer 25, if desired. Optic portion 21 is illustratively described as comprising three layers, although it will be apparent that other arrangements may be employed.

Haptic portion 22 illustratively comprises haptics 28 and 29 that extend from substrate 27. Each of haptics 28 and 29 includes an interior volume 30 that communicates with channel 31 in substrate 27. Actuator 24 is disposed in well 32 formed in intermediate layer 25 and substrate 27, so that a lower end of the actuator seats within well 32. Haptics 28 and 29 may each include a resilient support member 33 (see FIGS. 4 and 5) that urges the haptic radially outward to ensure that the haptic seats against the capsular equator.

Although channel 31 and well 32 are depicted in FIG. 5 having their side walls disposed parallel to the optical axis of the lens, it is expected that all such surfaces may be arranged obliquely relative to the optical axis of the IOL. Such an arrangement is expected to reduce the potential to create spurious reflections in light passing along the optical axis of the IOL. It should be understood that such arrangements may be beneficially employed throughout the IOLs described in this specification.

As depicted in FIG. 4, each of haptics 28 and 29 has an accommodated state and may be transitioned to an unaccommodated state (shown in dotted line in FIG. 4) by application of compressive forces to the anterior/posterior surfaces of the haptic (shown by arrows A) and reduction of radial compressive forces to the lateral surfaces of the haptic (shown by arrows B). Haptics 28 and 29 are configured so that the interior volumes of the haptics increase as the haptics deform from the accommodated state to the unaccommodated state. The accommodated state depicted by the solid lines in FIG. 4 corresponds to a fully-contracted state of the ciliary muscles, as described herein below.

Actuator 24 is disposed in well 31 of intermediate layer 25 and substrate 27, and preferably comprises a sturdy elastomeric material. Intermediate layer 25 isolates fluid in channel 31, well 32 and the interior of actuator 24 from the fluid disposed in the space 34 between anterior lens element 23 and intermediate layer 25. Fluids disposed within channels 31 and space 34, preferably comprise silicone or acrylic oils or other suitable biocompatible fluids, and are selected to have refractive indices that match the materials of anterior lens element 23, actuator 24, intermediate layer 25 and posterior lens element, i.e., substrate 27.

Illustratively, actuator 24 comprises a bellows structure integrally formed with anterior lens element 23, and is configured to deflect anterior lens element 23 responsive to fluid pressure applied within the bellows by haptics 28 and 29. Alternatively, actuator 24 may be fabricated as a separate component and glued or otherwise bonded to anterior lens element 23 and intermediate layer 25.

Deflection of the anterior lens element resulting from movement of actuator 24 cause the anterior lens element to transition between an accommodated state, in which the lens surface is more convex, to an unaccommodated state, in which the lens surface is less convex. As will of course be understood, optic portion could instead be arranged so that actuator 24 deflects posterior lens element 27. Still further, the actuator may be configured to induce a major deflection of one lens element and a minor deflection of the other lens element; the arrangement depicted in FIGS. 3 is intended to be illustrative only.

The inner surface and thickness of anterior element 23 (relative to the optical axis of the lens) are selected so that the outer surface of anterior element 23 retains an optically corrective shape throughout the entire range of motion of actuator 24, e.g., for accommodations 0-10 diopters. It should of course be understood that the inner surface and thickness of anterior element 23 may be selected to provide an aspherical outer surface, as required for a desired degree of optical correction.

While IOL 20 includes single actuator 24 located at the center of optic portion 21, the IOL alternatively may include an array of actuators spaced apart in a predetermined configuration on the posterior surface of the anterior lens element, as may be required to impose a desired pattern of localized deflection on the anterior lens element. As will be apparent to one of skill in the art, an annular structure may be substituted for the individual actuator depicted in FIG. 5, and the side walls of the actuator may be of any suitable shape other than a bellows structure. For example, the actuator may comprise a polymer that had been treated, such as by application of bi-axial stress, to pre-orient the polymer to stretch predominantly in a desired direction.

IOL 20 also may include coating 35 disposed on all interior fluid-contacting surfaces within the IOL, such as fluid channel 31 and well 32 and the surfaces defining space 34. Coating 35 is configured to reduce or prevent diffusion of the index-matched fluid used to drive actuator 24, and within space 34, from diffusing into the polymer matrix of the lens components and/or to prevent inward diffusion of external fluids into the IOL. The IOL also may include coating 36, which comprises the same or a different material than coating 35, disposed on the exterior surfaces of the lens. Coating 36 is intended to serve as a barrier to prevent the diffusion of fluids from the eye into the IOL or from the IOL into the eye, and may be disposed on the entire exterior surface of the optic portion and haptic portion, including the anterior and posterior lens elements and haptics.

Alternatively, both coatings 35 and 36 may be layered onto a single surface to prevent or reduce both ingress of bodily fluids into the IOL or fluid circuit, and loss of index-matched fluid from the interior spaces of the IOL. Coatings 35 and 36 preferably comprise a suitable biocompatible polymer, perfluorinated hydrocarbon, such as PTFE, inorganic (e.g., silicone dioxide) or metallic layer (e.g., nickel-titanium) applied by any of a variety-of methods known in the art.

Operation of IOL 20 of FIGS. 3-5 is now described. IOL 20 is implanted within a patient's capsule after extraction of the native lens using any suitable technique. When implanted, haptics 28 and 29 support the IOL so that optic portion 21 is centered along the central axis of eye. When the ciliary muscles are in a contracted state, the zonules are less taut and the capsule places radial compressive force on haptics 28 and 29 and haptics 28 and 29 are placed in the accommodated state. In this condition, fluid pressure applied by the fluid in the haptics, channel 31 and well 32 maintain actuator 24 fully extended, so that anterior lens element 23 is deflected to its accommodated state.

When the ciliary muscles relax, the zonules pull the capsule taut, thereby applying axial compressive forces on the anterior/posterior surfaces of the haptics and reducing the radial compressive forces on the lateral surfaces of the haptics. These force changes cause the haptics to deform to the unaccommodated state depicted by the dotted lines in FIG. 4, thereby increasing the interior volume of the haptics. Because there is only a predetermined amount of fluid contained within the interior of the haptics, channel 31, well 32 and actuator 24, the increased volume arising in unaccommodated haptics 28 and 29 draws fluid from within actuator 24. This in turn causes the actuator to shorten, deflecting anterior lens element 23 to a flatter, unaccommodated state. Subsequent contraction and relaxation of the ciliary muscles causes the foregoing process to repeat, thereby providing a degree of lens accommodation that mimics the accommodating action of the natural lens.

In the course of developing IOL 20 described above, it was observed that haptic design created the potential for movement of the entire haptic relative to the lens capsule and optic portion. It was theorized that such movement in turn might reduce the efficiency by which loads imposed by the lens capsule are converted to the hydraulic forces developed within IOL 20. The present invention therefore is directed to structure, which may be implemented in IOL 20, to more efficiently convert movements of the lens capsule into hydraulic forces for inducing movement of actuator 24 of the above-described device.

It was expected that because the anterior wall of the human lens capsule generally has a greater thickness than that of the posterior wall and may include more zonular attachments as the eye ages, the lens capsule may impose asymmetric loads on the IOL when transitioning between the accommodated and unaccommodated configurations. Accordingly, translation of the anterior wall towards the capsular equator was expected to be greater than that of the posterior wall when the capsule transitions between the unaccommodated and accommodated configurations.

Figure 6B:
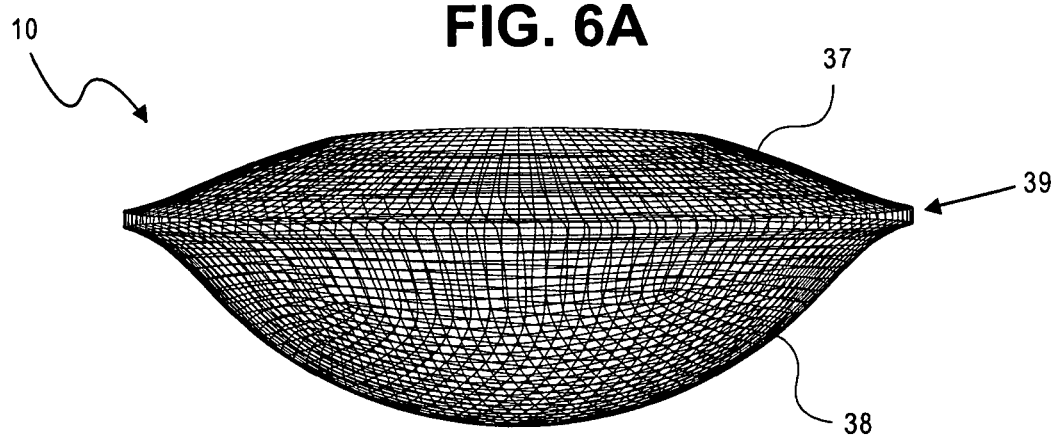
Figure 6C:
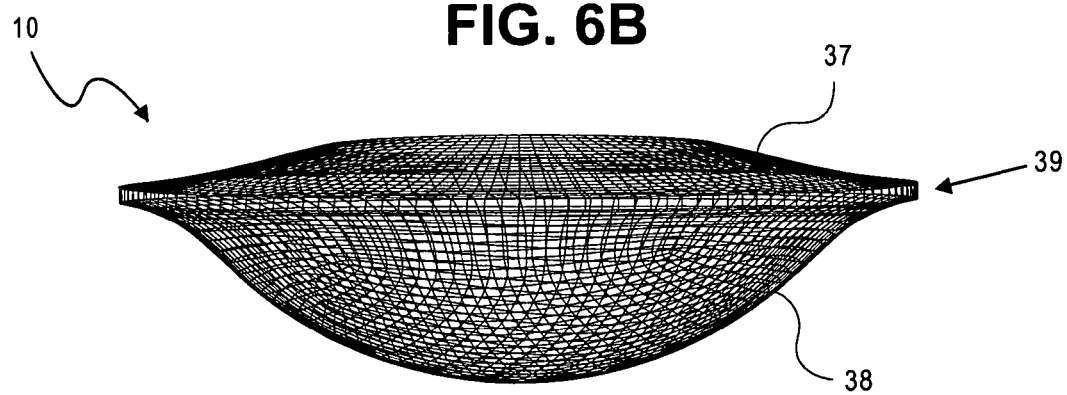

FIGS. 6A-6C illustrate the results of a numerical simulation of a lens capsule transitioning between the unaccommodated and accommodated configurations responsive to relaxation of ciliary muscles 13. In FIG. 6A, lens capsule 10 is fully accommodated and assumes its most highly convex shape. Anterior wall 37 extends generally convex upward and posterior wall 38 extends generally convex downward; the anterior and posterior wall portions are joined at equatorial portion 39.

In FIG. 6B, lens capsule 10 is depicted in an intermediate position between the fully accommodated and the fully unaccommodated configurations. In this case anterior wall 37 and posterior wall 38 are partially retracted towards equatorial portion 39 and equatorial portion 39 expands radially outward. As a result, each of anterior wall 37 and posterior wall 38 is less convex than in FIG. 6A.

In FIG. 6C, lens capsule 10 is shown in the fully unaccommodated configuration, with anterior wall 37 and posterior wall 38 further retracted toward equatorial portion 39 and equatorial portion 39 further expanded radially outward. The periphery of anterior wall 37, closest to equatorial portion 39, translates a significantly greater distance than the peripheral portion of the posterior wall that is equidistant from equatorial portion 39. As a result, the anterior wall is expected to exert significantly greater force upon a haptic near the equatorial portion 39 of the lens capsule than the posterior wall.

Figure 7A:
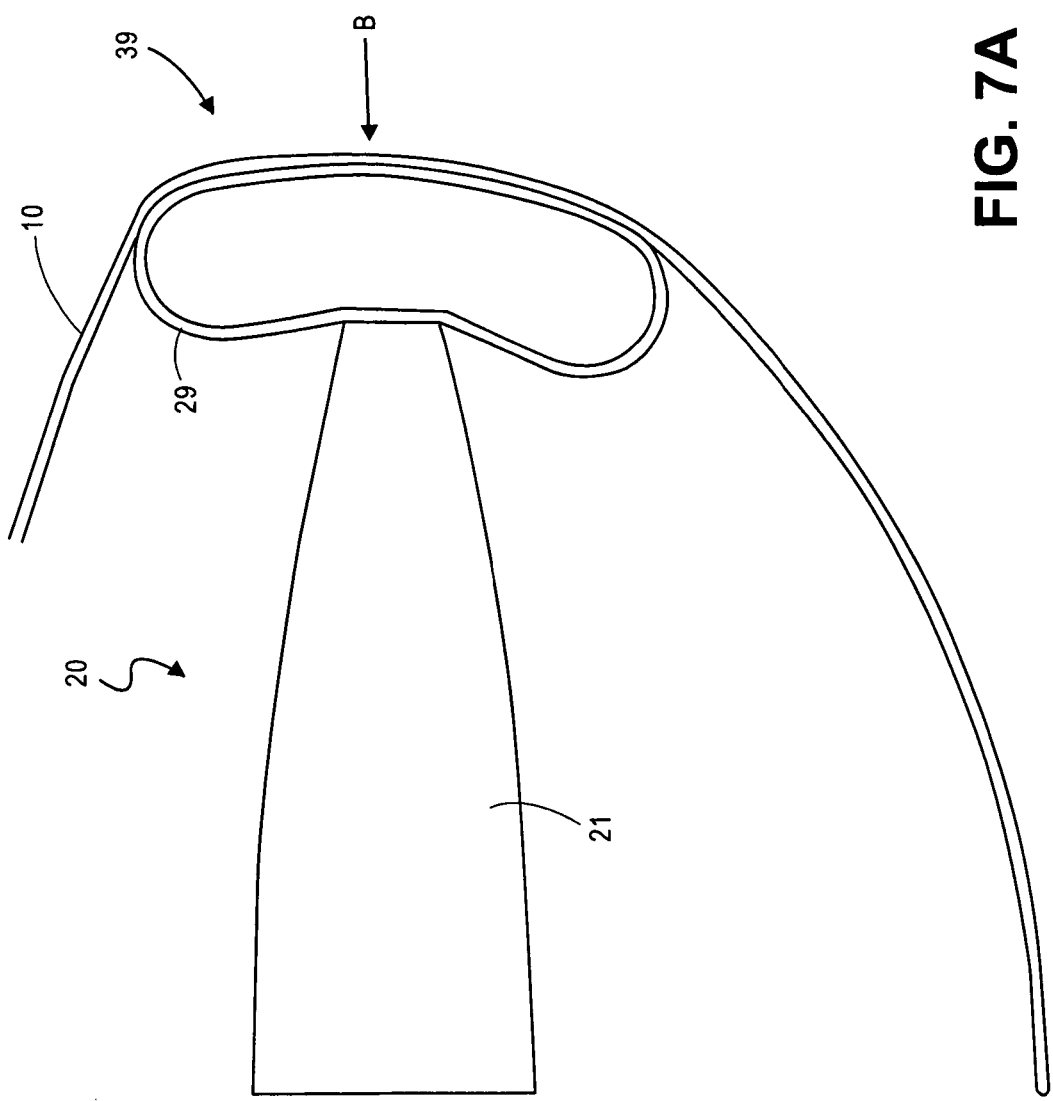

Referring to FIGS. 7A-7D, the interaction between lens capsule 10 and IOL 20 will be described in greater detail. FIG. 7A depicts the interaction between haptic 29 and lens capsule 10 when lens capsule 10 is in an accommodated state, corresponding to FIG. 6A. In such a state, compressive forces applied by lens capsule 10 upon haptic are generally directed radially inward toward the optical axis of IOL 20, as shown by arrow B. In such a configuration, haptic 29 is compressed between equatorial portion 39 of lens capsule 10 and optic portion 21 of IOL 20 such that a part of optic portion 21 forms a backstop. It should be appreciated, however, that the backstops disclosed herein may be formed from optic portion 21 and/or haptic portion 22 and/or separate structures.

When lens capsule 10 transitions to an intermediate position, as shown in FIGS. 6B and 7B, the radial force applied by lens capsule 10 on haptic 29 is reduced and a compressive force applied to the posterior/anterior faces of haptic 29 by lens capsule 10 is increased. It will be appreciated that the during the change in orientation of the compressive force acting on haptic 29 by lens capsule 10 there may be a period during which the volume of haptic 29 remains unchanged. However, that period may be reduced or eliminated, if desired, by tailoring the flexibility of haptic 29 and/or the configuration of a backstop and/or haptic 29.

Referring to FIG. 7C, lens capsule 10 is shown in a fully unaccommodated state. In the unaccommodated state, the radial compressive forces applied by lens capsule 10 upon haptic 29 are removed and lens capsule applies compressive forces on posterior/anterior faces of haptic 29. Those compressive forces further change the shape of haptic 29 so that the interior volume of haptic 29 increases.

As mentioned above, the transition from radial to posterior/anterior compressive force applied by lens capsule 10 on haptic 29 may result in an intermediate period of constant interior volume of haptic 29. Referring to FIG. 7D an alternative embodiment of haptic 29 is shown that includes a flange, or blade, 26. Flange 26 extends radially outward from a lateral surface of haptic 29 and contacts equatorial portion 39 of lens capsule 10. Flange 26 increases the radial compression of haptic 29 when lens capsule 10 is in an accommodated state. Because of that increased radial compression there is a greater change in interior volume of haptic 29 that will occur through the same motion of lens capsule 10. As a result, the period of constant interior volume of haptic 29 during the transition from the accommodated to the unaccommodated states may be reduced or eliminated.

Figure 8A:
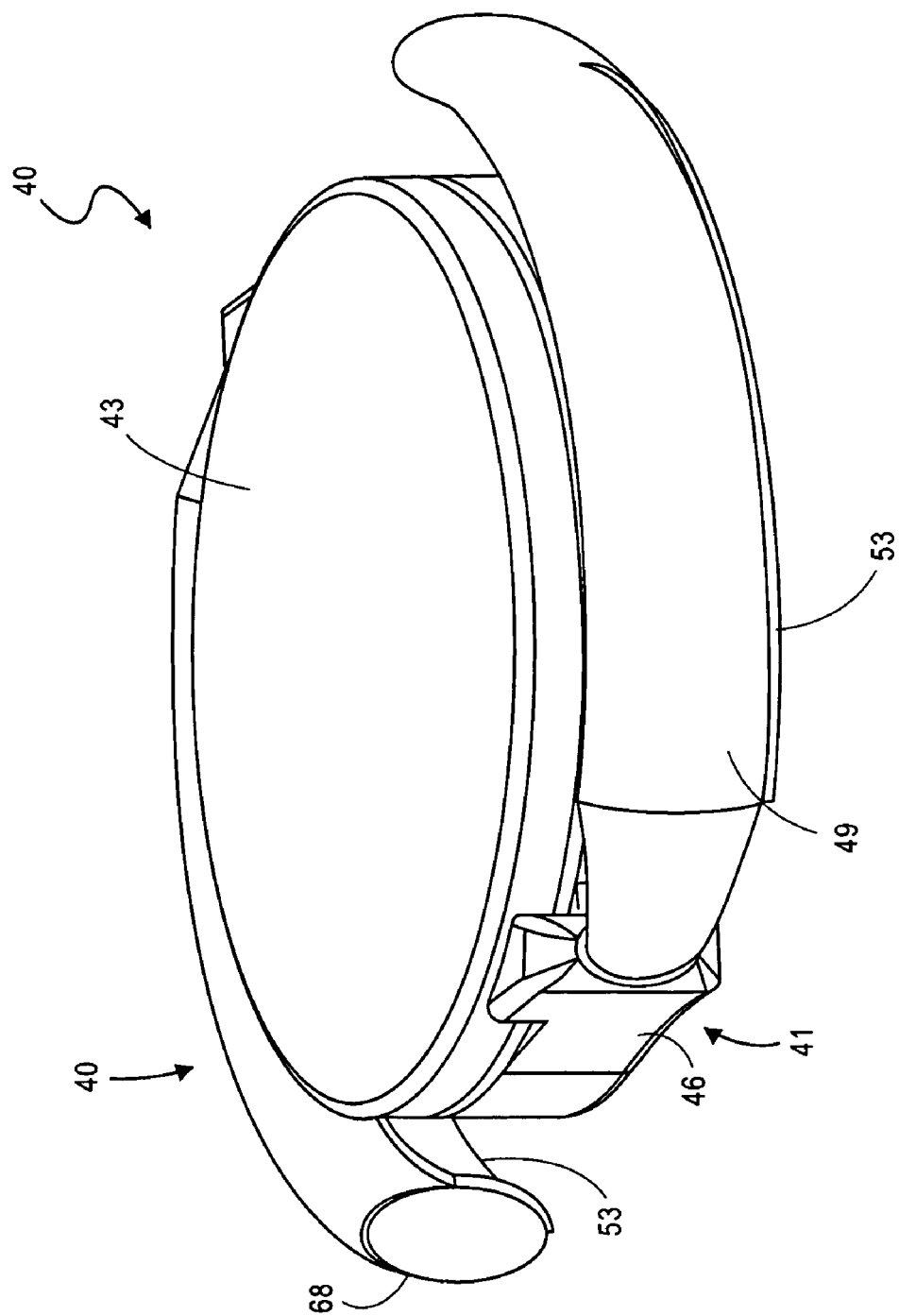
FIGS. 8A-8B are, respectively, a perspective view and a cross-sectional view of an illustrative embodiment of the intraocular lens of the present invention.
Figure 8B:
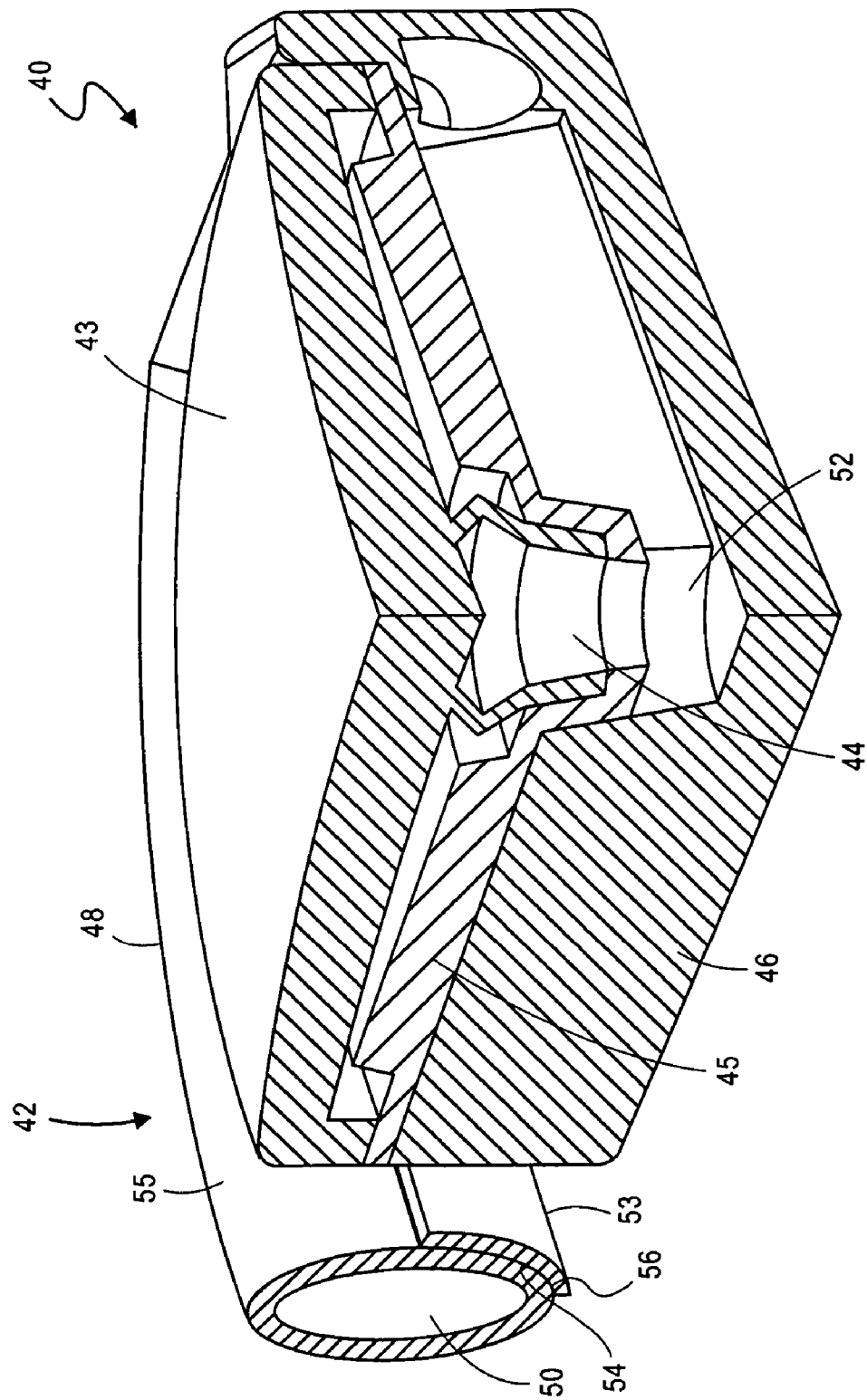

Referring now to FIGS. 8A and 8B, an embodiment of an IOL constructed in accordance with the principles of the present invention is described. IOL 40 seeks to maximize the hydraulic forces generated by the asymmetric loads imposed during transition of the lens capsule between the accommodated and unaccommodated configurations. IOL 40 generally includes optic portion 41 and haptic portion 42, both of which are similar in construction to the corresponding portions of the embodiment of FIGS. 3-5. In particular, optic portion 41 includes anterior lens element 43, actuator 44, intermediate layer 45 and substrate 46.

Haptic portion 42 includes haptics 48 and 49, each of which define interior volume 50 that is in fluid communication with channels and well 52 that are formed in substrate 46. Because the structure of the components is substantially identical to the corresponding structures of IOL 20 described above, these components will not be described in further detail.

In accordance with the principles of the present invention, IOL 40 further comprises backstops 53 that rigidly support at least a portion of the circumference of each of haptics 48 and 49. Haptic contact surfaces 54 of backstops 53 are coupled to a portion of the outer surface of each haptic 48, 49. Backstop 53 may be a cantilevered member that generally follows the substantially toroidal shape of the respective haptic. The portion of the circumference of each haptic 48 and 49 supported by backstop 53 is chosen so that it is diametrically opposed from the portion of the haptic that contacts the anterior wall and/or equatorial portion of the lens capsule. Anterior end 55 of haptic contact surface 54 ends approximately at the midline of haptic 48, i.e., midway between the extreme anterior and the extreme posterior surfaces of the haptic. Posterior end 56 of haptic contact surface 54 extends to the extreme posterior portion of the haptic such that approximately one quarter of the outer surface of haptic 48 is supported by the backstop.

During transition from the fully accommodated to the unaccommodated state, the anterior and posterior walls of the capsule retract toward the equatorial portion of the lens capsule and compress the haptic axially while the equatorial portion moves radially outward. As described above with reference to FIGS. 6A-6C, the portion of the anterior wall of the lens capsule translates a greater distance than the corresponding portion of the posterior wall. The anterior wall therefore is expected to impose a sufficiently large compressive load to actuate IOL 40. Backstop 53 provides a rigid surface that harnesses the asymmetric loads generated by the lens capsule during transition between the accommodated and unaccommodated configurations.

Haptics 48 and 49 and backstops 53 may be configured so that haptics are placed only in apposition (i.e., side by side contact) to the inner face of the anterior wall, so that the increased motion of the anterior wall may be fully utilized.

Alternatively, these components may be configured so that a portion of each haptic is placed in apposition to the inner face of the anterior wall while another portion is placed in apposition to an inner face of the posterior wall of the lens capsule.

Backstop 53 may be constructed from any suitable biocompatible material known in the art. For example, backstop 53 may be constructed from a suitable biocompatible polymer having a relatively higher rigidity than the haptic it supports. For example, backstop 53 may comprise a stiffer material or have a greater thickness or have a three dimensional structure that provides this higher rigidity. Backstops 53 may be injection molded, machined, heat or pressure formed from a sheet material, or by any other method known in the art. Each of backstops 53 may be coupled to a respective haptic with a biocompatible adhesive, ultrasonic welding, or any other method known in the art. Backstops 53 also may each include a flexible, foldable or hinged portion substantially adjacent to optic portion 41 of IOL 40, which permits the backstops to be folded inward to simplify insertion into the lens capsule.

Figure 9A:
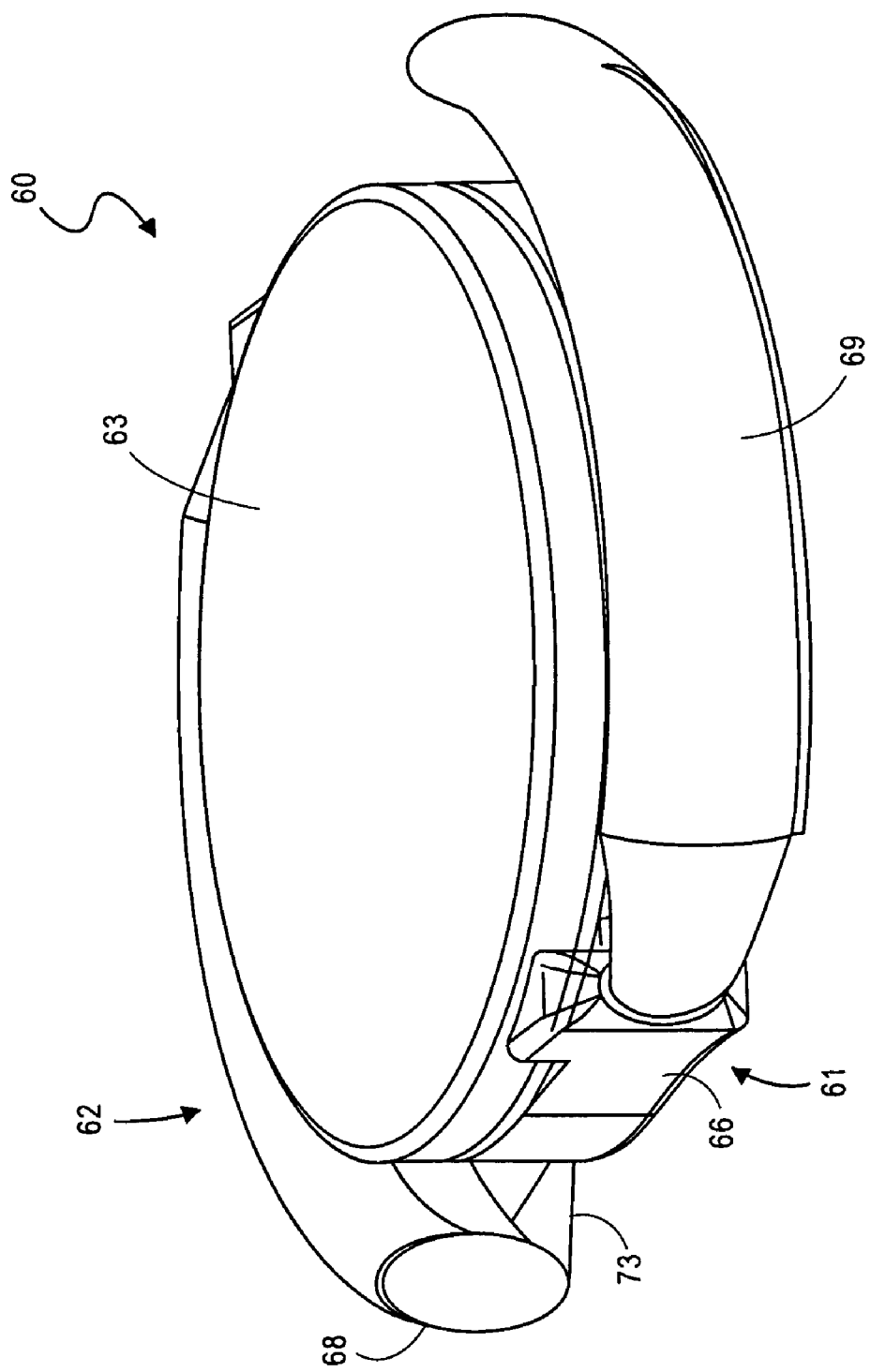
FIGS. 9A-9B are, respectively, a perspective view and a cross-sectional view of an alternative embodiment of the intraocular lens of the present invention.
Figure 9B:
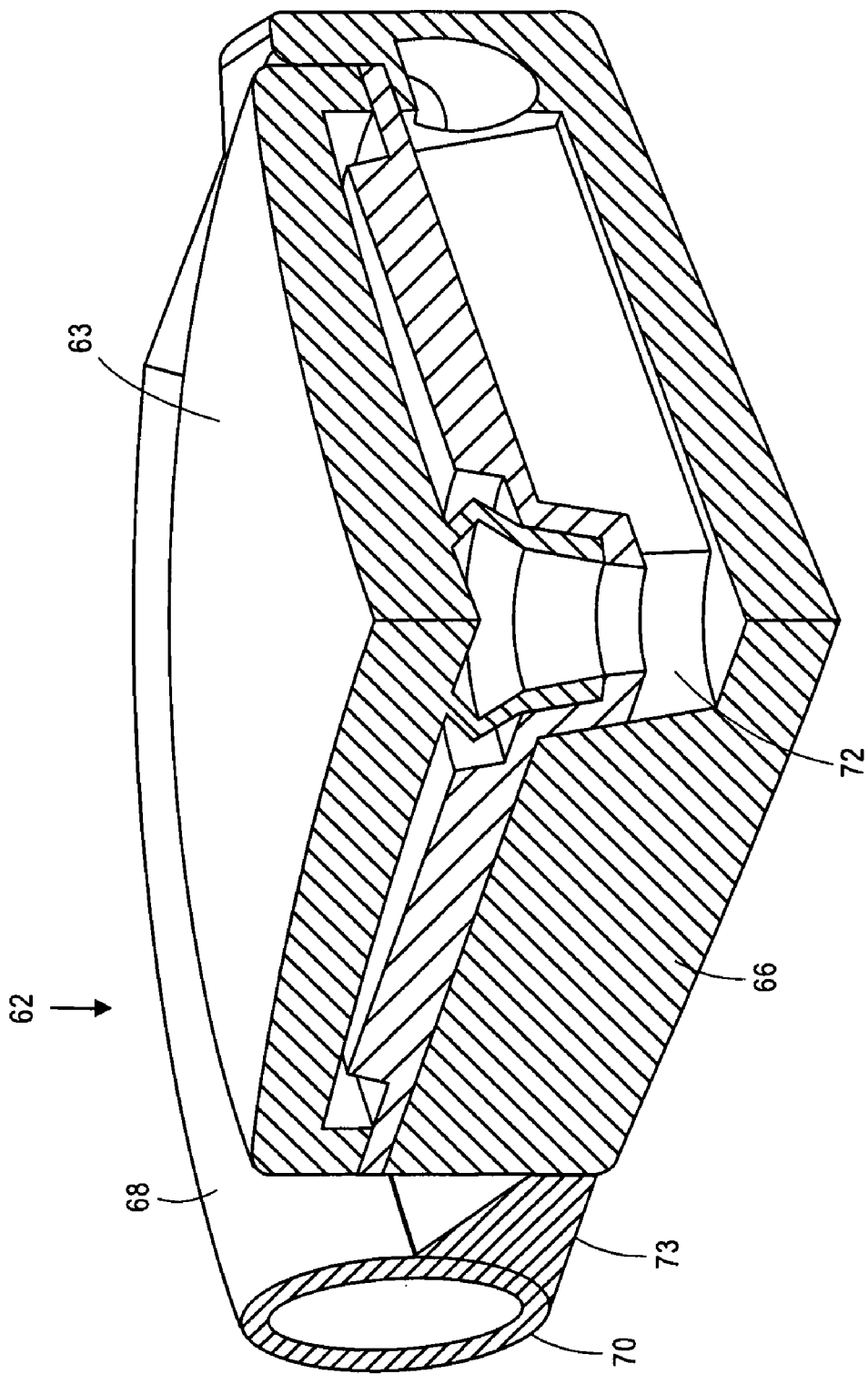

Referring now to FIGS. 9A and 9B, an alternative embodiment of an IOL constructed in accordance with the principles of the present invention is described. IOL 60 generally includes optic portion 61 and haptic portion 62, both of which are similar in construction to the corresponding portions of the embodiments described above. In particular, optic portion 61 includes anterior lens element 63, actuator 64, intermediate layer 65 and substrate 66.

Haptic portion 62 includes haptics 68 and 69, each of which define interior volume 70 that is in fluid communication with channels and well 72 that are formed in substrate 65. Because the structure of the components is substantially identical to the corresponding structures of the previously described embodiment these components will not be described in further detail.

Backstops 73 also are provided in IOL 60, and extend from optic portion 61 to haptics 68 and 69. Backstops 73 may be generally shaped as sections of a disk or cone. It will be appreciated that although backstops 73 are shown as a solid member, the backstops also may include cavities or may have a web-like construction. It will be further appreciated that backstops 73 may be constructed to facilitate implantation, and may include flexible, foldable or hinged sections. Alternatively, backstops 73 may be attached to optic portion 61 and haptic portion 62 after the components are inserted into the lens capsule.

Figure 10A:
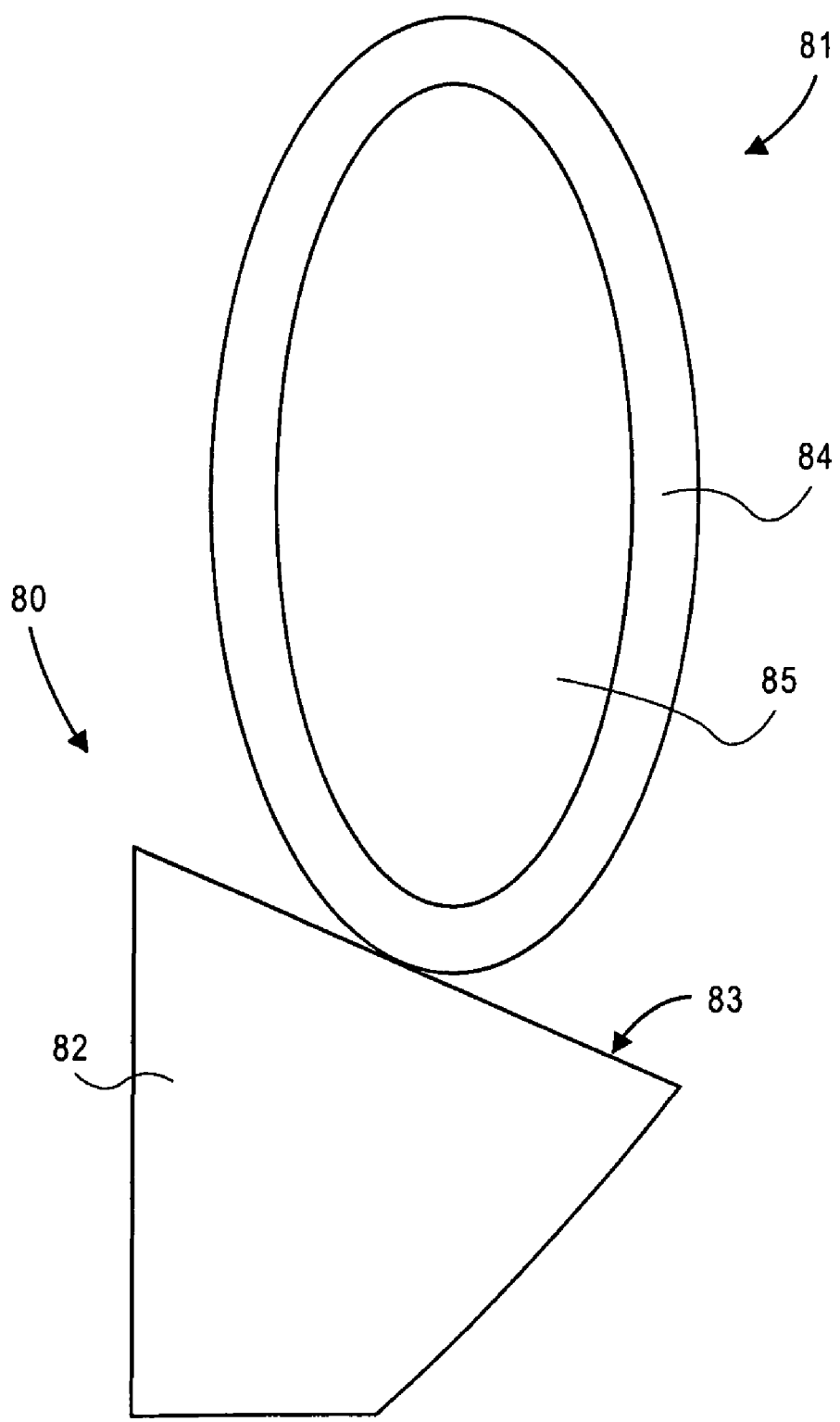
Figure 10B:
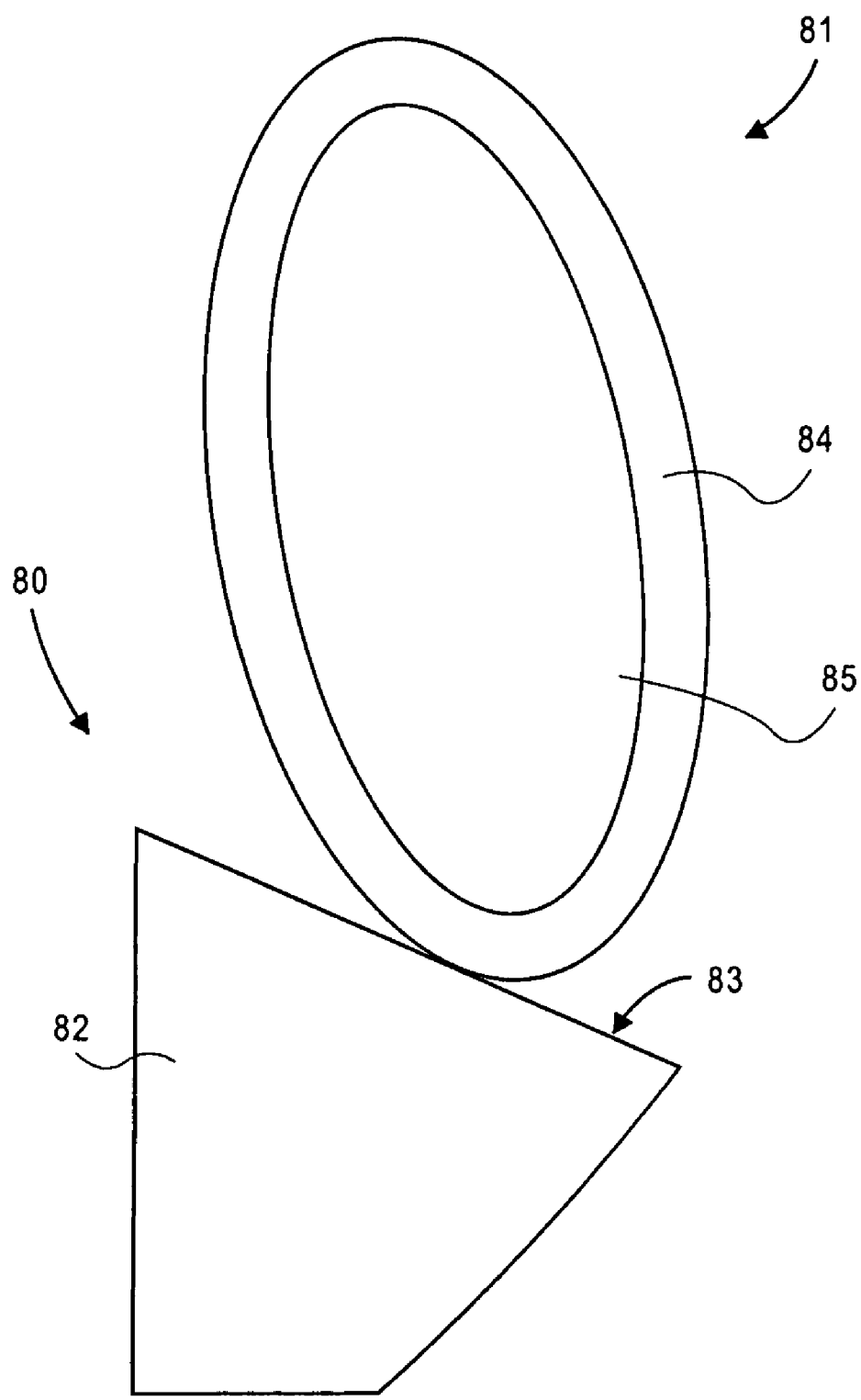
Figure 10C:
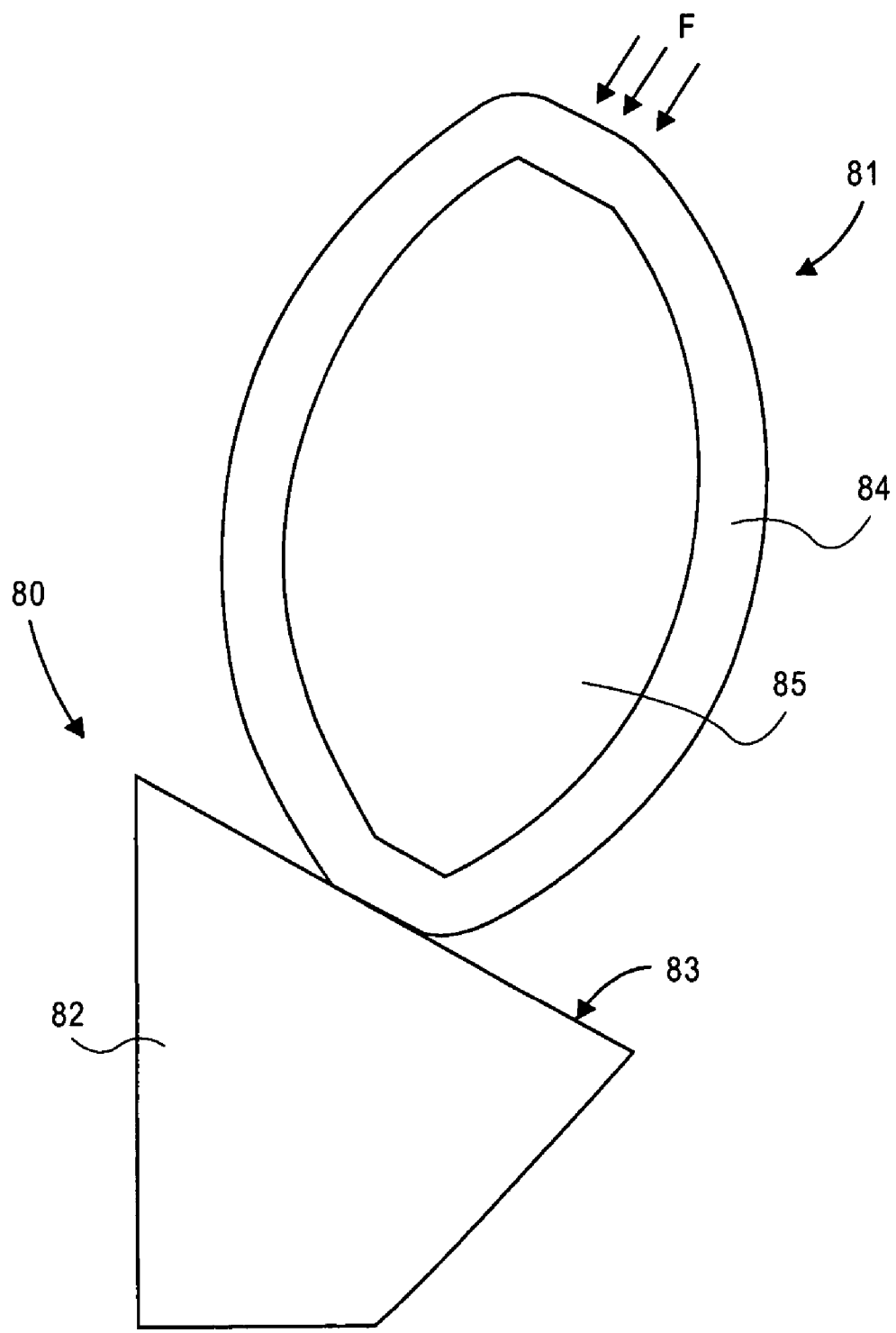

The backstops may be configured to support any portion of the circumference of the haptics so that they counteract compressive forces placed on the haptics in the anterior/posterior direction and/or the radial direction. In FIGS. 10A-10C, backstop 80 is configured to provide a tangential support to haptic 81. Backstop 80 includes body portion 82 and generally conical support surface 83 that is in tangential contact with outer surface 84 of haptic 81, when haptic 81 is in an accommodated or intermediate state. The orientation of haptic 81 with respect to backstop 80 may be selected to provide desired compression characteristics. For example, as shown in FIG. 10A, haptic 81 is oriented so that it has a major axis that is generally vertical, which generally corresponds to being parallel to the optical axis of the IOL. As shown in FIG. 10B, haptic 81 may be oriented so that it has a major axis that is rotated with respect to the optical axis. It should be appreciated that haptic 81 may be oriented-at any angle with respect to the optical axis of the respective IOL and the support surface 83 of the respective backstop 80. Support surface 83 of backstop 80 may be oriented such that support surface is cylindrical, conical or planar.

Once implanted and upon relaxation of the ciliary muscle, the lens capsule exerts compressive forces F on haptic 81 that cause deformation of haptic 81, as shown in FIG. 10C. Because the anterior wall of the lens capsule is expected to generate a larger force due to its larger translation near the equatorial portion, support surface 83 of backstop 80 preferably is configured to directly oppose those forces. Accordingly, backstop 83 is positioned to prevent translation of the haptic in response to forces applied by the anterior wall of the lens capsule. Support surface 83 is configured so that it is conical, oriented generally perpendicular to the direction of force F and located on a side of haptic 81 opposite from the anterior wall of the lens capsule. Tangential contact between accommodated haptic 81 and support surface 83 of backstop 80 will substantially deform haptic 81 during posteriorly-directed motion of the anterior wall of the lens capsule.

Figure 11A:
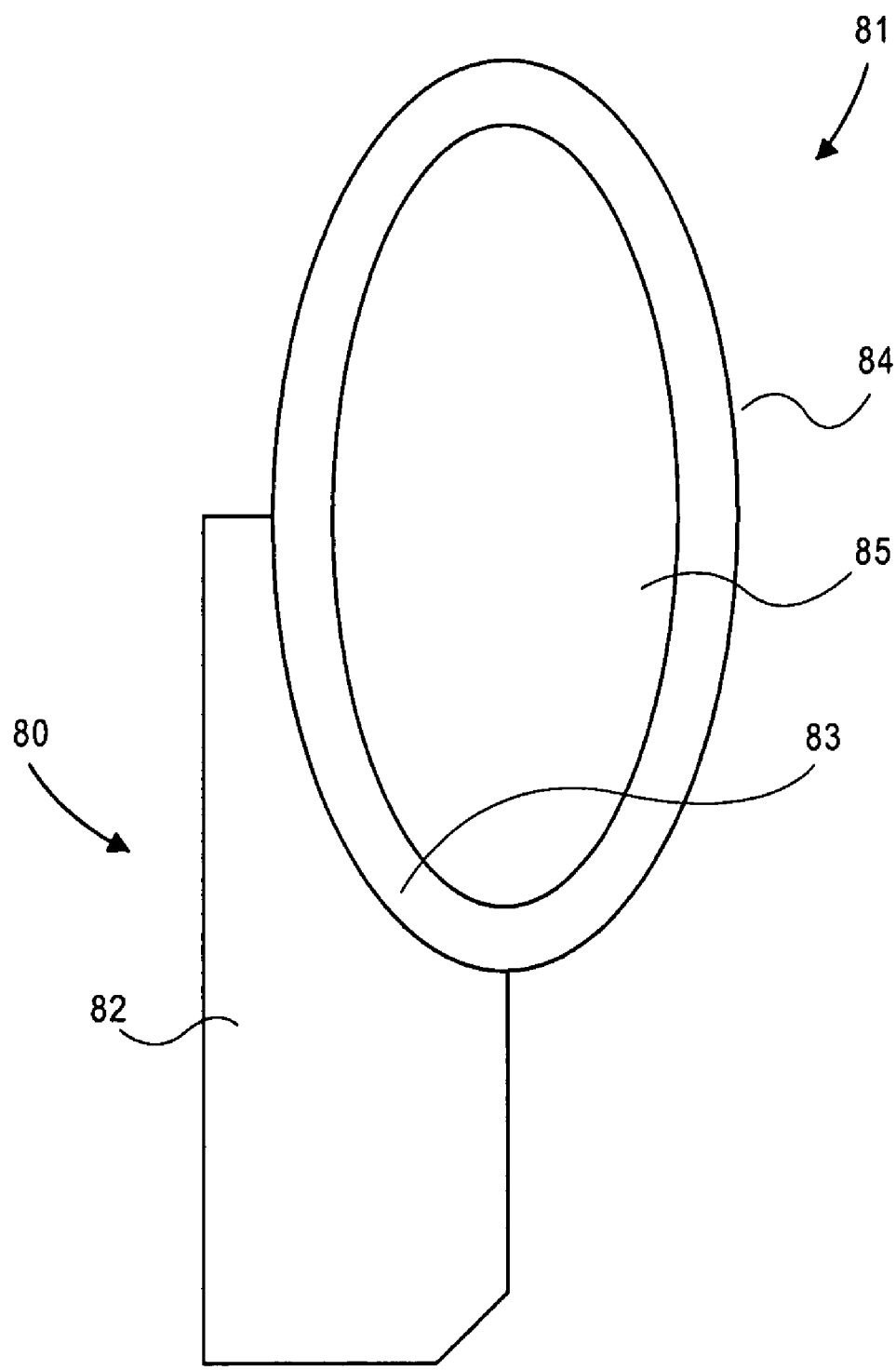
FIGS. 11A-11B are, respectively, cross-sectional schematic views of a backstop and a haptic in both accommodated and unaccommodated states.
Figure 11B:
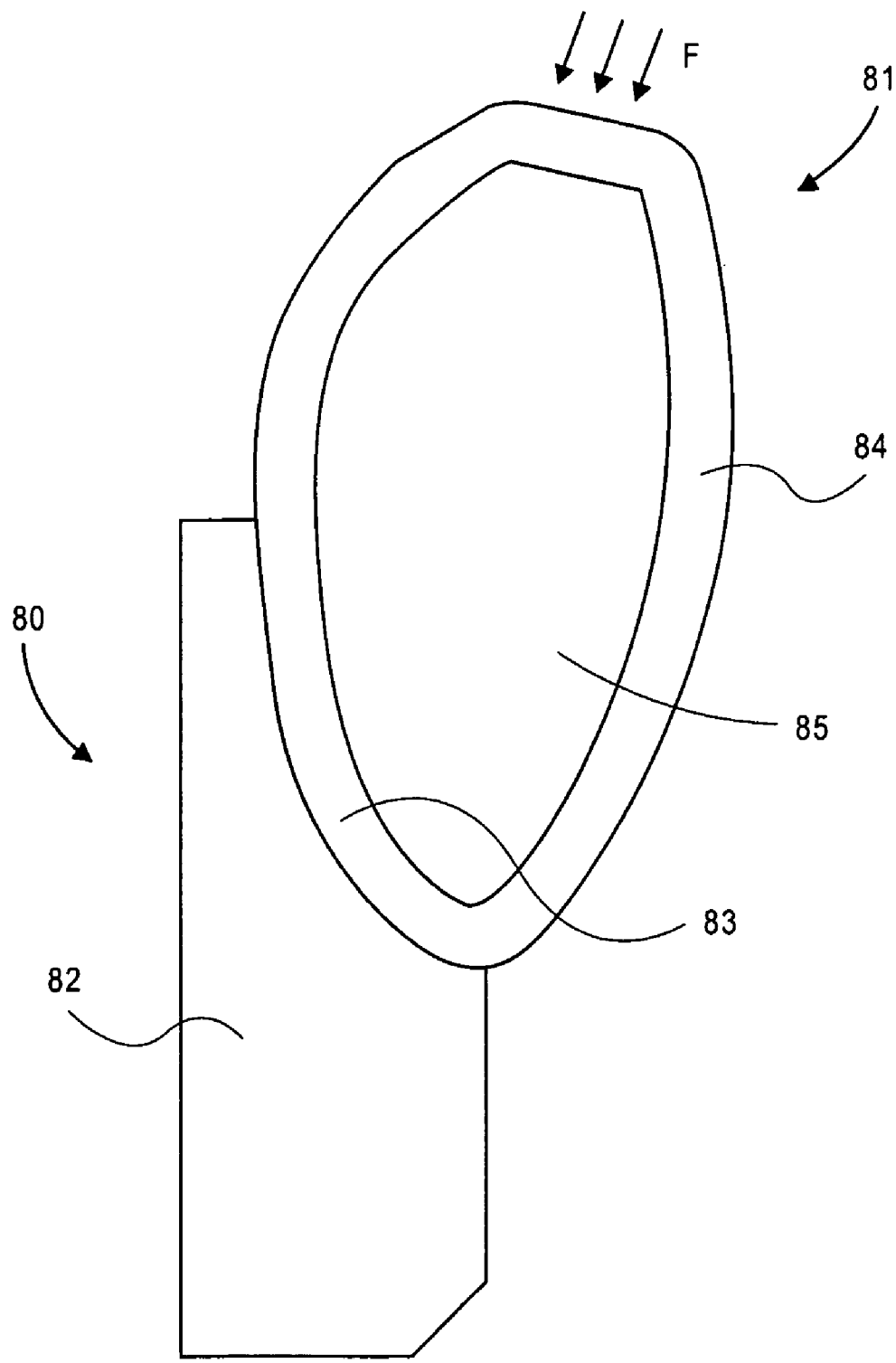

With respect to FIGS. 11A and 11B, another embodiment of backstop 80 is described that provides additional support to haptic 81. Backstop 80 includes a curved support surface 83 configured to generally match the curvature of outer surface 84 of haptic 81 in an accommodated state and to support a portion of the circumference of haptic 81. Illustratively, backstop 80 is configured to support approximately one quarter of outer surface 84 of haptic. It should be appreciated that haptic 81 may be oriented at any angle with respect to the optical axis of the respective IOL and the support surface 83 of the respective backstop 80.

The anterior wall of the lens capsule exerts forces F upon haptic 81 and backstop 80 prevents posteriorly-directed translation of haptic 81, thereby converting the compressive load applied by the lens capsule to a change in the hydraulic pressure and moving the lens actuator. The configuration of support surface 83 in FIGS. 11 maintains the supported portion of haptic 81 with a uniform shape, irrespective whether the haptic is in the accommodated or unaccommodated state. The amount of support provided by backstop 80 may be chosen for a desired deflection of haptic 81 between the accommodated and unaccommodated states.

Figure 12A:
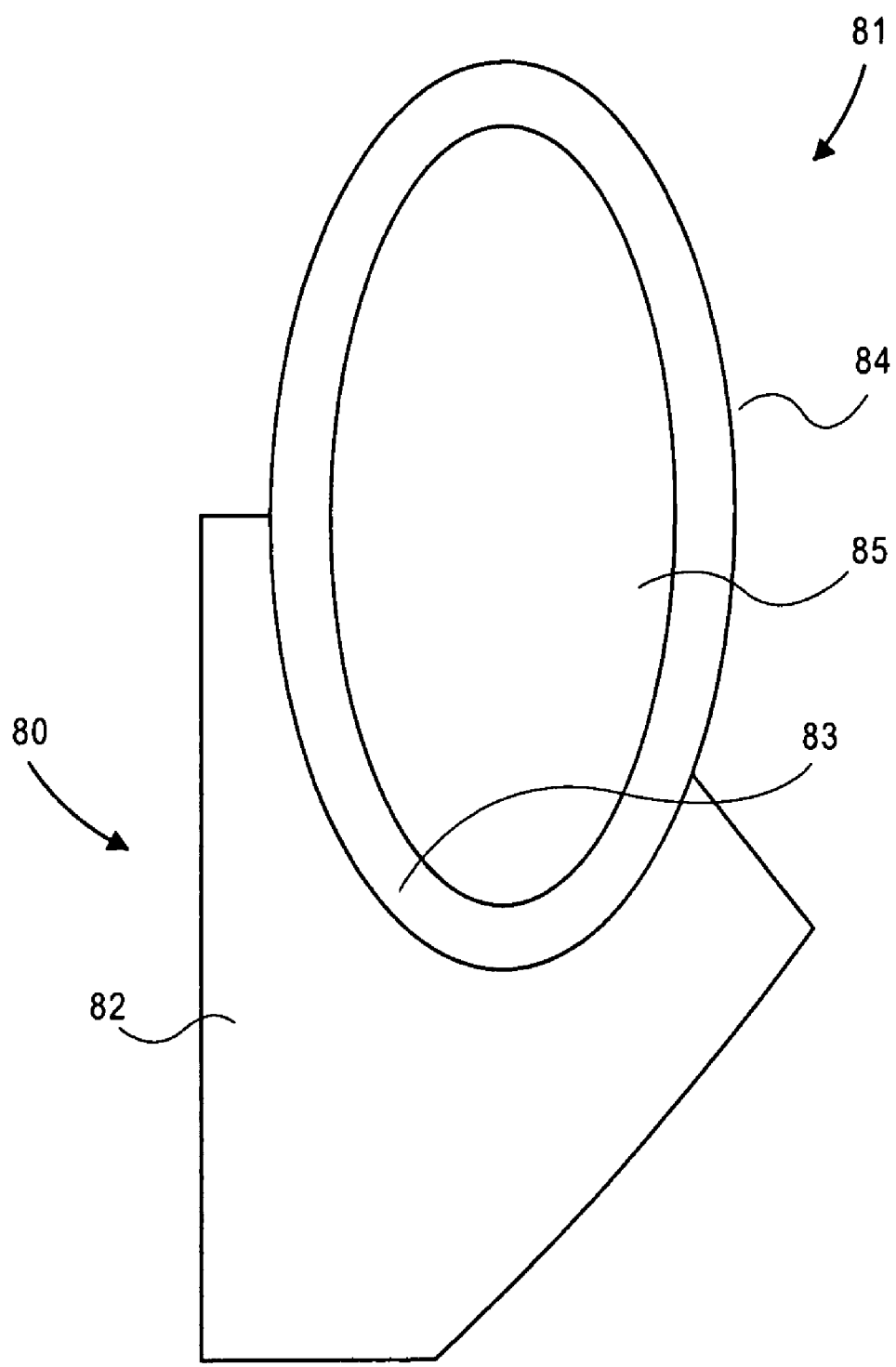
Figure 12B:
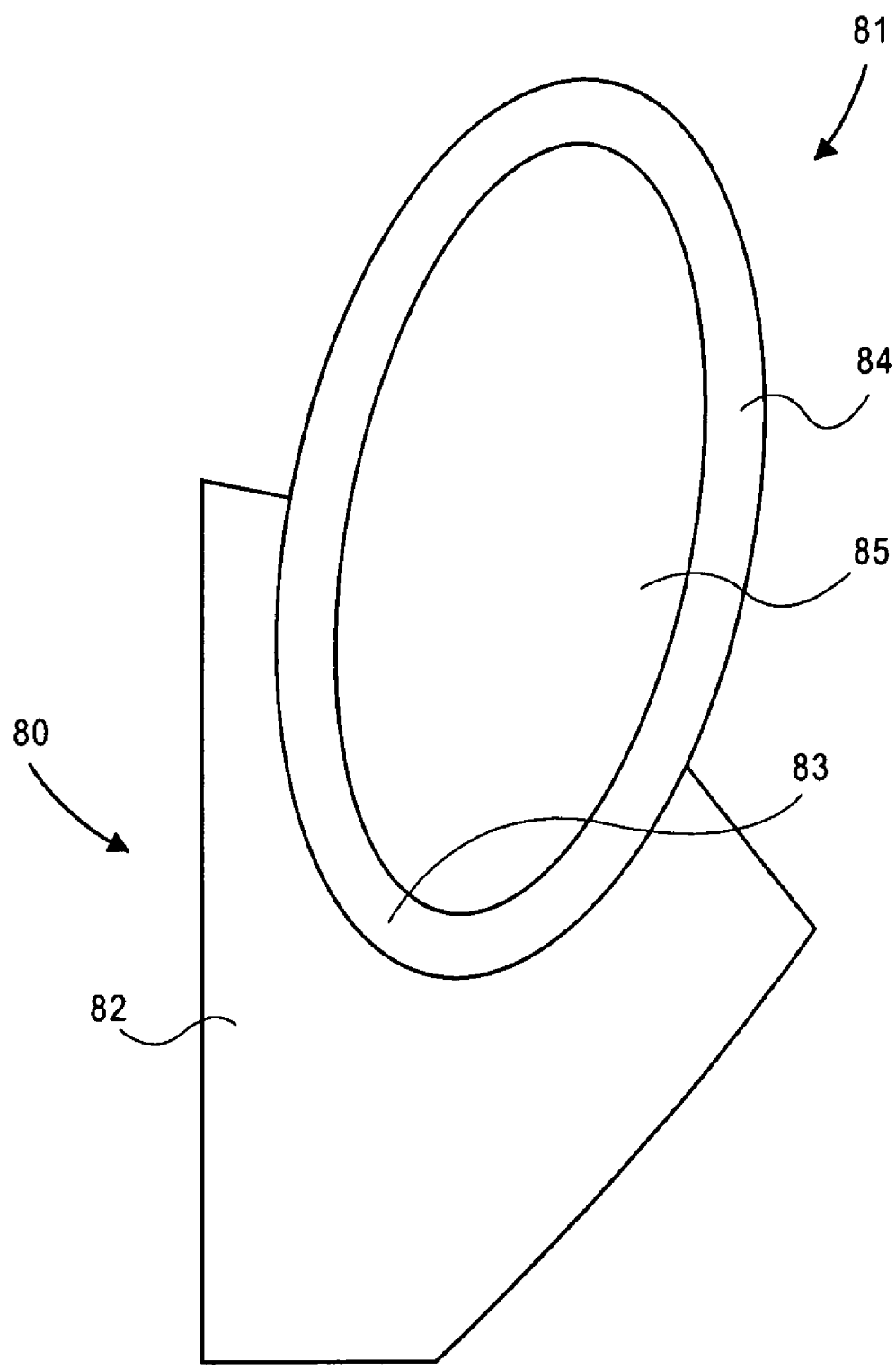
Figure 12C:
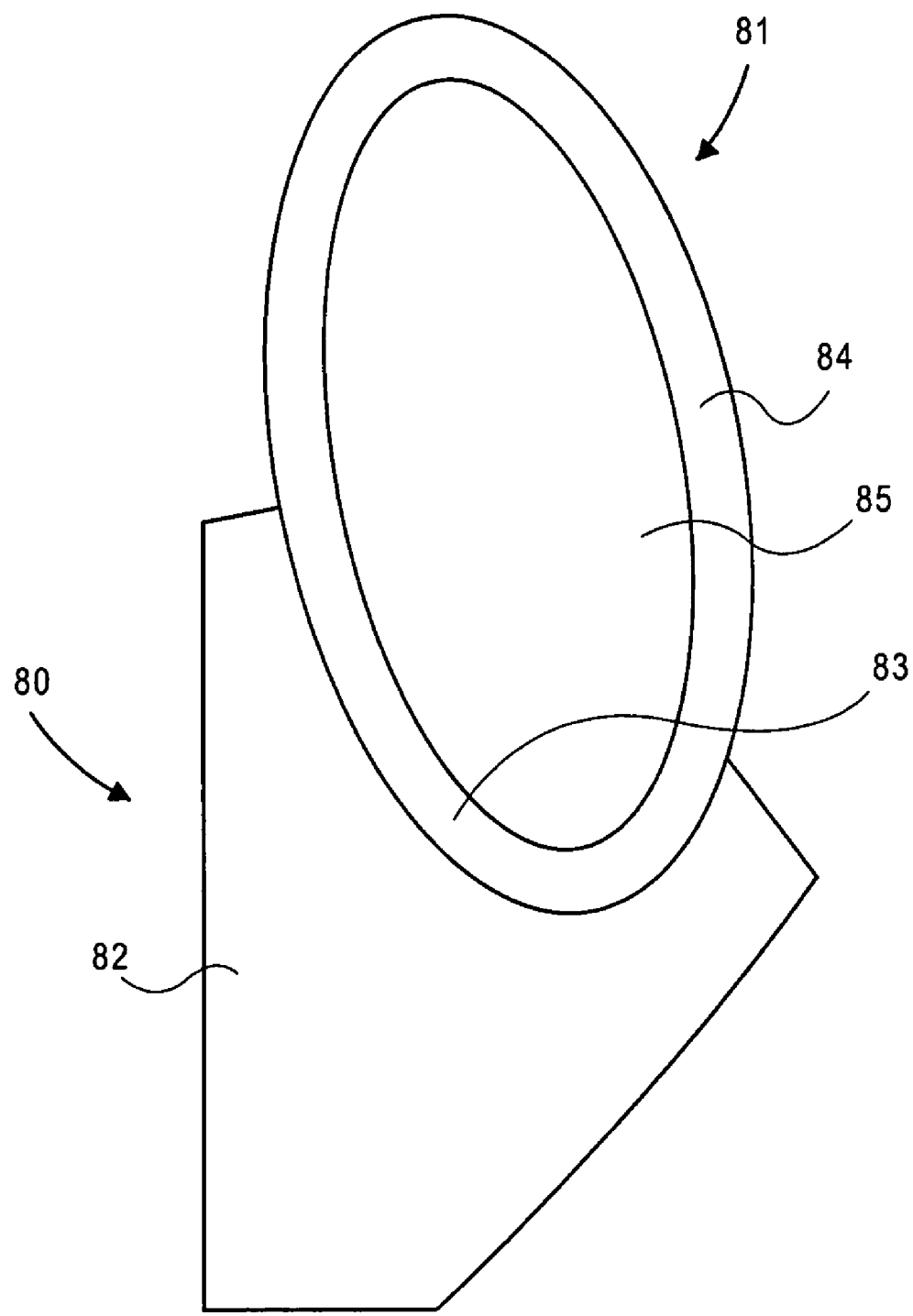
Figure 12D:
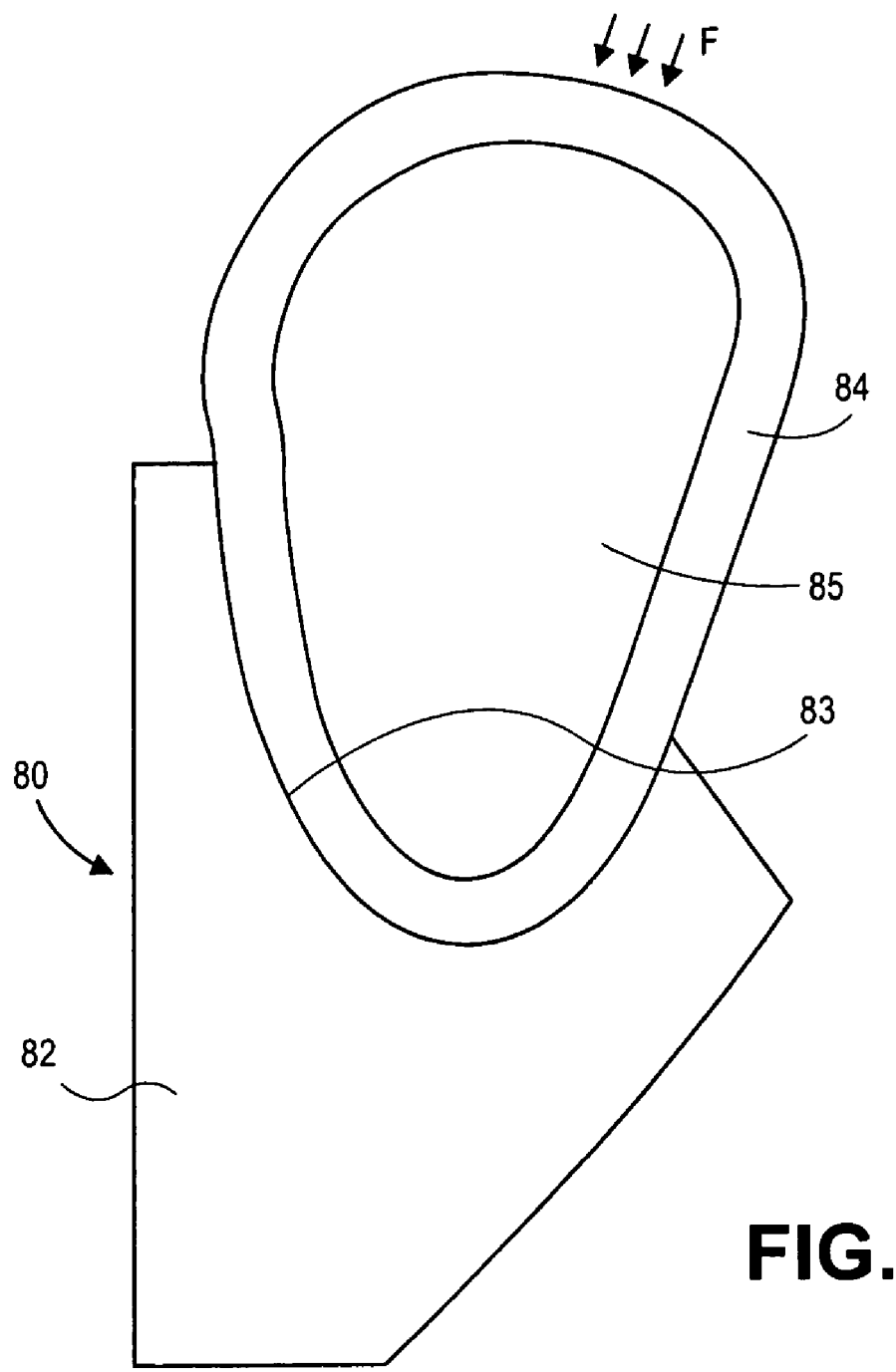

In yet another embodiment, depicted in FIGS. 12A-12D, a greater portion of haptic 81 is supported. In this embodiment backstop 80 is configured to support a relatively large interior and posterior portion of haptic 81. In particular, support surface 83 of backstop is configured to generally match the curvature of accommodated haptic 81 and to support approximately half of the outer surface 84 of haptic 81. It should be appreciated that the orientation of haptic 81 with respect to the optical axis of the respective IOL and the support surface 83 of the respective backstop 80 may be selected to provide desired compression characteristics. FIGS. 12A-12C illustrate various orientations of haptic 81 and FIG. 12D illustrates haptic 81 in an unaccommodated state.

Figure 13A:
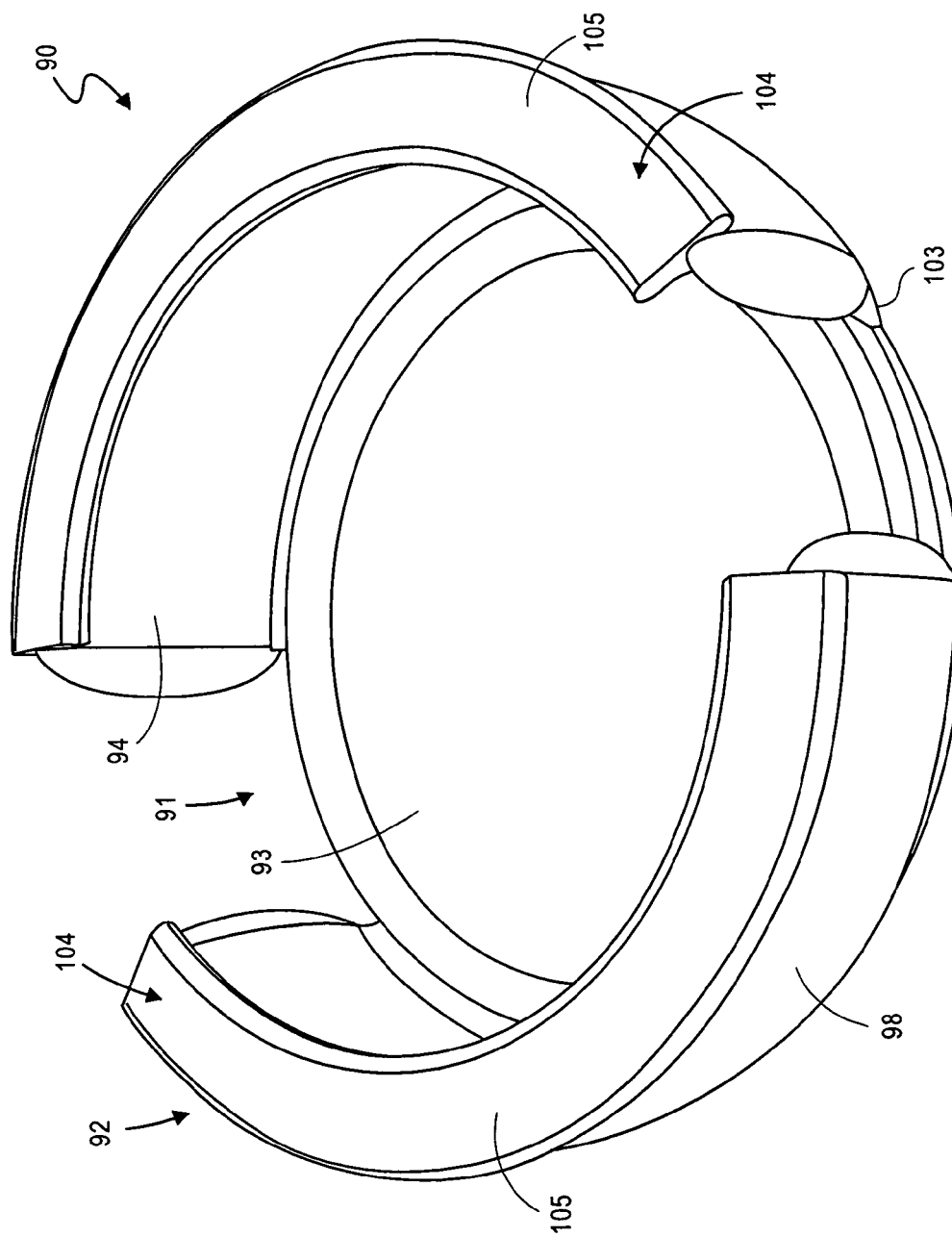
FIGS. 13A-13B are, respectively, a perspective view and a cross-sectional view of an alternative embodiment of the intraocular lens of the present invention.
Figure 13B:
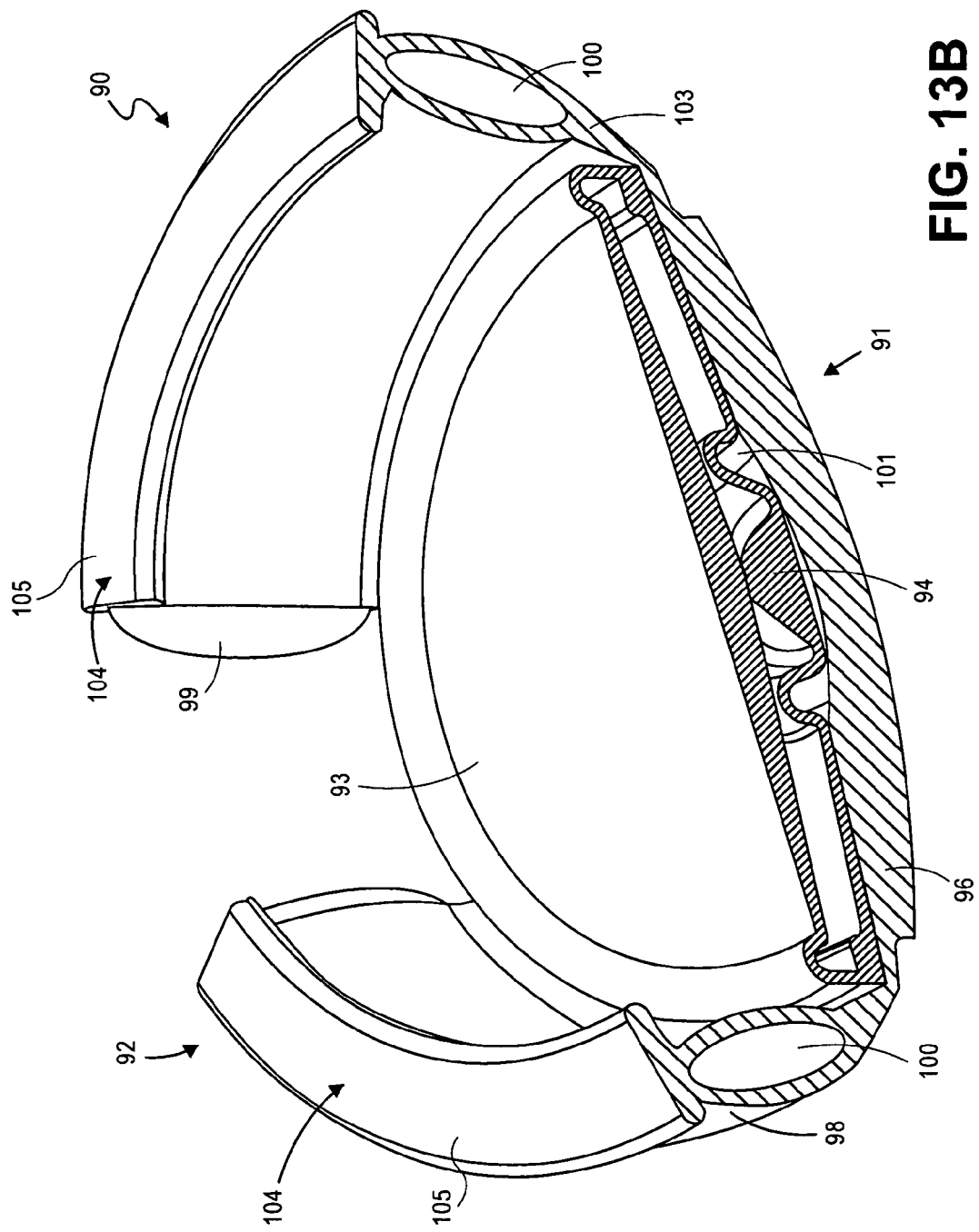

Referring to FIGS. 13A and 13B, an additional embodiment of an IOL constructed in accordance with the principles of the present invention is described. Similar to the previously described embodiments, IOL 90 generally includes optic portion 91 and haptic portion 92. Optic portion 91 includes anterior lens element 93, substrate 96 and actuator 94 interposed therebetween. In the present embodiment, actuator 94 also forms an intermediate layer and substrate 96 may function as a posterior lens element.

Haptic portion 92 includes haptics 98 and 99, each of which defines interior volume 100 that is in fluid communication with channels (not shown) and well 101 that are formed between actuator 94 and substrate 96. Each haptic 98, 99 is integrated into substrate 96 and extends backstop portion 103 of substrate 96. Backstop 103 is configured to provide support over a posterior portion of haptics 98, 99, similar to the support provided by the backstop shown in FIGS. 12A-12D. It should be appreciated that the dimensions of haptics 98 and 99 and backstop portion 103 are selected so that backstop portion 103 is significantly more rigid than haptics 98, 99.

Additionally, load shelf 104 is provided on an anterior portion of each haptic 98, 99 that is approximately diametrically opposed to backstop 103. Shelf 104 includes anterior surface 105 that is configured to engage a portion of the anterior wall of a lens capsule. Anterior surface 105 provides a greater surface area upon which force may be exerted on haptic 98, 99 by the lens capsule. As a result, energy from movement of the capsular bag may be captured more efficiently and converted into deformation of haptic 99, 98 and hydraulic forces within IOL 90.

It should be appreciated that the backstops described herein may be formed as monolithic portions of any component of the respective optic portion, as shown in the embodiment of FIGS. 13A and 13B, or they may be separate components that are mechanically coupled to the respective optic portion, as shown in the embodiments of FIGS. 8 and 9.

In addition to utilizing backstops and/or load shelves and/or flanges to improve the efficiency with which an IOL converts movement of the lens capsule to hydraulic forces, spring forces throughout the IOL may be biased. In particular, the spring forces created by the various components of the IOL may be tailored by selecting the elasticities of the components accordingly so that the force applied by movement of the capsule may be amplified. For example, the elasticity of the haptic provides one spring force, and the combined return force of the anterior lens and actuator provides another spring force. The components may be selected so that one of those spring forces is stronger than the other. After the components are selected accordingly, the IOL may be charged with fluid during manufacture so that the fluid provides additional force that equalizes the unequal spring forces. Finally, introducing the IOL into a lens capsule may introduce an additional bias force. As a result, energy is stored in the IOL that may be released during use to reduce the force that is required from movement of the capsule actuate the IOL. In an exemplary embodiment, the anterior lens may be formed so that in a relaxed state it is in an unaccommodated configuration and the haptic may be formed so that in a relaxed state it is in an accommodated state. The pressure of the fluid may also be used to shift the bias toward either the accommodated or unaccommodated state.

It will be appreciated that the backstop of the foregoing embodiments may have a modular construction. For example, backstop may be implanted-and then the optic and haptic portions may be subsequently implanted as a unit and coupled to the backstop. This arrangement may simplify the implantation procedure by allowing the IOL to be further compressed, thereby reducing the size of the incision needed to implant the IOL.

A plurality of modular backstops 80, having different configurations and providing different amounts of support, also may-be provided with an optic portion and a haptic portion in a kit. Such a kit may be provided so that the amount of interior volume change of the associated haptic may be selected by choosing a specific configuration of backstop. For example, if a maximum change in interior volume is desired, a backstop providing tangential contact with a haptic may be chosen. Conversely, if a minimum change in interior volume is desired, a backstop configured to provide additional support may be selected. Such a kit also may be provided so that an IOL may be custom fit to the anatomy of a particular patient.

The support configurations of backstop 80 and haptic 81 described above are configured for a haptic that transitions between a small internal volume in the accommodated state and a larger internal volume in the unaccommodated state. It should be appreciated, however, that use of the backstop is not limited to this specific configuration of haptic. Instead, the haptic may have a cross-sectional shape that provides any desired change in interior volume between the fully accommodated and fully unaccommodated states. Accordingly, the present invention also may be used with haptics that decrease in volume when the haptic transitions from the fully accommodated state to the fully unaccommodated state.

It further will be appreciated that the backstop may include stiffening members. For example, stiffening members may be molded into backstops or otherwise coupled to backstops. Furthermore, such stiffening members may comprise any material known in the art having a greater modulus of elasticity than the backstop. A backstop also may be located such that it counteracts the forces placed on the haptic by the posterior wall of the capsular bag, for example, where the forces applied by the posterior wall of the capsular bag are sufficient to actuate the intraocular lens.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An intraocular lens comprising:
an optic portion including a lens element configured to be deflected between an accommodated configuration and an unaccommodated configuration, wherein the optic portion includes an optical axis extending in an anterior to posterior direction; and
a haptic having an interior volume filled with a fluid, wherein the haptic is in fluid communication with the optic portion,
wherein the haptic is configured such that movement of the capsular sac changes the interior volume of the haptic and wherein a first portion of the haptic is adapted to engage the capsular sac, wherein the haptic, at a location in the first portion, has a cross-sectional configuration in a non-stressed configuration in a plane extending in the anterior to posterior direction in which a maximum linear anterior-to-posterior dimension between any two points on an outer surface of the haptic is greater than a maximum linear radial dimension between any two points on an outer surface of the haptic, and
wherein the lens element is configured to change curvature in response to changes in the interior volume of the haptic such that it transitions between the accommodated state and the unaccommodated state.

2. The intraocular lens of claim 1 wherein the haptic is a first haptic, the intraocular lens further comprising a second haptic with an interior volume filled with the fluid, the second haptic is in fluid communication with the optic portion.

3. The intraocular lens of claim 1 wherein the fluid is adapted to be moved between the haptic and the optic portion in response to changes in the interior volume of the haptic.

4. The intraocular lens of claim 1 wherein the cross sectional configuration is an oval.

5. The intraocular lens of claim 1 wherein the volume of fluid in the haptic is larger when the optic is in an unaccommodated configuration than when the optic is in an accommodated configuration.

6. The intraocular lens of claim 1 wherein an anterior-most portion of the haptic extends further in the anterior direction than an anterior-most portion of the optic portion.

7. The intraocular lens of claim 1 wherein the optic portion includes an actuator layer in between an anterior layer and a posterior layer.

8. The intraocular lens of claim 1 wherein the haptic has a radially inner portion that is less flexible than a radially outer portion.

9. An intraocular lens comprising:
- an optic portion including a lens element configured to be deflected to change the power of the intraocular lens, wherein the optic portion includes an optical axis extending in an anterior to posterior direction; and
- a haptic having an interior volume with a fluid therein, wherein the interior volume is in fluid communication with the optic portion,
- wherein the haptic is configured such that movement of the capsular sac changes the interior volume of the haptic and wherein a first portion of the haptic is adapted to engage the capsular sac, wherein the haptic, at a location in the first portion, has a cross-sectional configuration in a non-stressed configuration in a plane extending in the anterior to posterior direction in which a maximum linear anterior-to-posterior dimension between any two points on an outer surface on the haptic is greater than a maximum linear radial dimension between any two points on an outer surface of the haptic,
- wherein the lens element is configured to change curvature in response to changes in the interior volume of the haptic such that it transitions between the accommodated state and the unaccommodated state, and
- wherein the haptic has a radially inner portion that is less flexible than a radially outer portion.

* * * * *

UNITED STATES PATENT AND TRADEMARK OFFICE
CERTIFICATE OF CORRECTION

| | | |
|---|---|---|
| PATENT NO. | : 8,361,145 B2 | Page 1 of 1 |
| APPLICATION NO. | : 11/642388 | |
| DATED | : January 29, 2013 | |
| INVENTOR(S) | : Scholl et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1133 days.

Signed and Sealed this
Eighteenth Day of November, 2014

Michelle K. Lee
*Deputy Director of the United States Patent and Trademark Office*